United States Patent [19]

Mercer et al.

[11] Patent Number: 4,860,584
[45] Date of Patent: Aug. 29, 1989

[54] COMPOSITE MOISTURE SENSING APPARATUS AND METHOD

[75] Inventors: William C. Mercer, Brookfield, Conn.; Peter K. Coughlin, Yorktown Heights, N.Y.; Donald McLeod, Jr., Briarcliff Manor, N.Y.; Edith M. Flanigen, White Plains, N.Y.

[73] Assignee: UOP, Des Plaines, Ill.

[21] Appl. No.: 213,239

[22] Filed: Jun. 29, 1988

[51] Int. Cl.$^4$ ............................................. G01N 1/00
[52] U.S. Cl. ................................................. 73/336.5
[58] Field of Search ................. 502/65, 67, 69, 214; 73/336.5, 29

[56] References Cited

U.S. PATENT DOCUMENTS

| 3,186,225 | 6/1965 | Freeman, Jr. | 73/336.5 |
| 4,791,083 | 3/1988 | Pellet et al. | 502/64 |
| 4,814,316 | 3/1989 | Pellet et al. | 502/214 |

Primary Examiner—Carl F. Dees
Attorney, Agent, or Firm—Thomas K. McBride

[57] ABSTRACT

A moisture sensing element is disclosed which comprises an electrically continuous article comprising a multi-compositional, multi-phase composite composition comprising as phases thereof (i) an electrically conducting or semiconducting substrate, (ii) an inorganic oxide composition layer in proximity to at least a portion of the surface of the electrically conducting or semiconducting substrate and (iii) an inorganic crystalline molecular sleeve composition layer upon at least a portion of the surface of the inorganic oxide composition layer, wherein the different phases of the composite composition are substantially contiguous and exhibit at least one of a distinct compositional heterogeneity and a distinct structural heterogeneity of one phase to the other; and at least one electrode affixed to the article in current carrying relationship so that the current carried by the electrode passes through at least a portion of the inorganic crystalline molecular sieve composition layer.

70 Claims, 1 Drawing Sheet

COMPOSITE MOISTURE SENSING APPARATUS AND METHOD

BACKGROUND OF THE INVENTION

This invention relates to a method of and apparatus for measuring the moisture content of a fluid system. More particularly, it relates to a moisture sensing element constructed of certain crystalline materials for use in such a method and apparatus.

The detection of the amount of water in a fluid stream is often of importance, e.g., in environmental and process control. Examples of areas where knowledge of the amount of water entrained in a stream are important include, but are not limited to, heating and air conditioning systems, dry gas streams, drying ovens and chemical reactions. Humidity sensors, to be effective, should have high sensitivity and selectivity, temperature insensitivity or compensation, good reversibility, fast response, highly stable response, infrequent need for calibration, and should tolerate corrosive and high temperature environments. The range of moisture levels which need to be detected may range from ppm or lower to 100% relative humidity. Moisture can be present in a fluid stream as water vapor, steam or present in a non-aqueous liquid. The term "fluid system" as used herein is intended to include air and other gases containing water and also liquids containing a small amount of water.

One useful category of instruments which may be employed to sense moisture in fluid systems are the electric hydrometers. As used herein, an electric hydrometer is an instrument for determining the moisture content of a fluid system by measuring or determining the electric impedance, or related property, of a hygroscopic material as an indication of the humidity or water content of the fluid system. By "electrical impedance" or "impedance" is meant that quantity as classically defined which takes into account at least one, and preferably both, of the electrical resistance and the electrical capacitance of a material or an electrical circuit. In instances where the electrical resistance of a material is very small, the electrical impedance measured is substantially the reciprocal electrical capacitance of the material. Conversely, where the capacitance of the material is very large, the electrical impedance measured is substantially the electrical resistance of the material. The term "electrical impedance" or "impedance" may include only electrical resistance or reciprocal electrical capacitance, provided that such value is a valid indicator of the humidity or water content of the fluid system being analyzed.

Zeolite molecular sieves are crystalline materials with a large and well defined interior volume. Access to this interior volume is controlled by openings, or pores, in the crystal. Molecules in the liquid or gas phase are adsorbed into the zeolite molecular sieves selectively on the basis of their size and polarity, among other things. Zeolite molecular sieves are aluminosilicates which contain charge balancing cations in the pore volume. These cations are mobile and thus render the zeolite molecular sieves ionic conductors.

Zeolite molecular sieves identified as zeolites X, A, Y, T, R, D, L, S, G, chabazite, erionite, faujasite, mordenite and analcite have been disclosed as humidity sensors in U.S. Pat. No. 3,186,225, which is incorporated in its entirety herein by reference. This patent discloses that the mobility of framework cations is a function of polar adsorbates and thus the resistance of a pressed powder compact of such zeolite molecular sieves equipped with electrodes can be monitored as a function of variable humidity levels. This patent also discloses that the lowest possible impedance gives the best results. The impedance of these systems decreases as the number and mobility of the charge balancing cations increases. In general, the zeolites disclosed in this patent have silica to alumina molar ratios of less than 6. Thus, the zeolite sodium X is preferred in this patent.

SUMMARY OF THE INVENTION

A new moisture sensing element has been discovered. It has been found that certain composite compositions comprising an inorganic crystalline composition layer or layers provide substantial advantages. For example, the composite compositions useful in the present invention are surprisingly sensitive to small changes in moisture content and exhibit good water adsorption-desorption reversibility. This latter property provides advantageously reduced response times to changes in moisture level. In addition, the presently useful composite compositions have good high temperature and hydrothermal stability. Further, the present, preferably relatively high impedance, systems often exhibit a linear or substantially linear response to temperature changes, thus, making compensating for such changes easier and more reliable. Moreover, the present sensing elements are structurally stable at high temperatures and/or in many corrosive environments.

In one broad aspect, the present invention involves a moisture sensing element comprising an electrically continuous article comprising one or more of certain multi-compositional, multi-phase composite compositions; and at least one electrode affixed to the article in current carrying relationship so that the current carried by the electrode passes through at least a portion of the inorganic crystalline composition layer of the composite. The presently useful composite compositions are fully disclosed in commonly assigned U.S. patent application Ser. No. 213,261, filed June 29, 1988 by W. C. Mercer, et. al. This application is incorporated in its entirety by reference herein. This sensing element may be a component of a hydrometer which further comprises an impedance measuring means connected to the electrode or electrodes for measuring the electrical impedance of at least a portion, e.g., a predetermined, controlled portion, of the sensing element.

In another broad aspect, the invention involves a method for measuring the water content of a fluid system. This method comprises immersing in the fluid system an electrically continuous sensing element, e.g., as described above. The electrical impedance of at least a portion of the sensing element is measured. This electrical impedance is correlatable to the moisture content in the fluid system. Thus, by knowing the impedance/moisture content relationship, e.g., obtained by prior calibration of the sensing element, one can, by measuring the electrical impedance, determine the water content of the fluid system.

DETAILED DESCRIPTION OF THE INVENTION

The present invention takes advantage of certain composite compositions, preferably with relatively high impedance, i.e., electrical impedance as that term is classically defined or in certain cases-as discussed previously-electrical resistance or reciprocal capacitance. The present moisture sensing elements are electrically continuous, i.e., are physically structured so that an electrical current can pass through the composite composition. The sensing element comprises a multi-compositional, multi-phase composite composition comprising as phases thereof: (i) an electrically conducting or semiconducting substrate; (ii) an inorganic oxide composition layer in proximity to at least a portion of the surface of the substrate; and (iii) an inorganic crystalline composition layer upon at least a portion of the surface of the inorganic oxide composition layer. The different phases of the composite composition are substantially contiguous and exhibit at least one of a distinct compositional heterogeneity and a distinct structural heterogeneity.

Among the inorganic crystalline compositions useful in the present invention are those often referred to as microporous molecular sieves. A particularly useful class of inorganic crystalline compositions are those selected from the group consisting of zeolite molecular sieves, preferably those having a molar ratio of silica to alumina greater that 6, more preferably greater than about 8; silica molecular sieves; non-zeolitic molecular sieves and mixtures thereof. In certain instances, the molecular sieves include one or more organic templating agents, which are often included during synthesis of these materials. These templating agents can be removed, e.g., by combustion. However, it should be noted that both molecular sieves with templating agents and molecular sieves without templating agents may be employed in the present invention.

Typical of the molecular sieves of the zeolitic varieties are the chabazite, faujasite, levynite, Linde Type A, gismondine, erionite, sodalite, Linde Type X and Y, analcime, gmelinite, harmotome, levynite, mordenite, epistilbite, heulandite, stilbite, edingtonite, mesolite, natrolite, scolecite, thomsonite, brewsterite, laumontite, phillipsite, ZSM-5 (U.S. Pat. No. 3,702,886), ZSM-20 (U.S. Pat. No. 3,972,983), ZSM-11 (U.S. Pat. No. 3,709,979), ZSM-12 (U.S. Pat. No. 3,832,449), ZSM-34 (U.S. Pat. No. 4,086,186), LZ-105 (U.S. Pat. No. 4,257,885) and Beta (U.S. Pat. No. 3,308,069 and U.S. Reissue Pat. No. 28,341), and the like. Typical of suitable zeolitic molecular sieves employable in the practice of this invention are those reviewed by Flanigen in Pure & Applied Chemistry Vol. 52 pp. 2191–2211 1980 including their ion exchanged forms. Zeolite ion exchange is reviewed by D. W. Breck in Chapter 7 of his book, "Zeolite Molecular Sieves", Wiley-Interscience, New York 1974. Also suitable are the zeolitic molecular sieves discovered since these reviews such as: LZ-210, LZ-211, LZ-212, etc. all from U.S. Pat. No. 4,503,023, EU-13, U.S. Pat. No. 4,581,211, ISI-6, U.S. Pat. No. 4,578,529, and the like including their ion exchanged forms.

Molecular sieves of the non-zeolitic variety include the silica molecular sieves, such as silicalite (U.S. Pat. No. 4,061,724) silicalite II (D. M. Bibby, et al., Nature, 1979, Vol. 280, pg. 664), and fluoride silicalite (U.S. Pat. No. 4,073,865).

Other molecular sieves of the non-zeolitic variety include these having an empirical chemical composition on an anhydrous basis expressed by the formula:

$$mR: (Q_wAl_xP_ySi_z)O_2 \qquad (I)$$

where "Q" represents at least one element present as a framework oxide unit "$QO_2^n$" with charge "n" where "n" may be $-3, -2, -1, 0$ or $+1$; "R" represents at least one organic templating agent present in the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of $QO_2^n$, $AlO_2^-$, $PO_2^+$, $SiO_2$, respectively, present as framework oxide units. "Q" is characterized as an element having a mean "T—O" distance in tetrahedral oxide structures between about 1.51 Angstroms and about 2.06 Angstroms. "Q" has a cation electronegativity between about 125 kcal/gm-atom to about 310 kcal/gm-atom and "Q" is capable of forming stable Q—O—P, Q—O—Al or Q—O—Q bonds in crystalline three dimensional oxide structures having a "Q—O" bond dissociation energy greater than about 59 kcal/gm-atom at 298° K.; and said mole fractions being within the limiting compositional values or points as follows:

w is equal to 0 to 98 mole percent;
y is equal to 1 to 99 mole percent;
x is equal to 1 to 99 mole percent; and
z is equal to 0 to 98 mole percent.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. The invention contemplates combinations of the elements as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of AlPO$_4$ as discussed below. Where z has a positive value, then the operative structure is that of SAPO, discussed below. Thus, the term QAPSO does not perforce represent that the elements Q and S (actually Si) are present. When Q is a multiplicity of elements, then to the extent the elements present are as herein contemplated, the operative structure is that of the ELAPSO or ELAPO or MeAPO or MeAPSO molecular sieves, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various non-zeolitic compositions and structures described hereinbelow.

NON-ZEOLITIC MOLECULAR SIEVES

The term "non-zeolitic molecular sieves" or "NZMS" is defined in the instant invention to include the "SAPO" molecular sieves of U.S. Pat. No. 4,440,871 and U.S. Ser. No. 575,745, filed Jan. 31, 1984, "ELAPSO" molecular sieves as disclosed in U.S. Ser. No. 600,312, filed Apr. 13, 1984, and certain "AlPO$_4$", "MeAPO", "FeAPO", "TAPO" and "ELAPO" molecular sieves, as hereinafter described. Crystalline "AlPO$_4$" aluminophosphates are disclosed in U.S. Pat. No. 4,310,440 issued Jan. 12, 1982, and in U.S. Ser. No. 880,559, filed June 30, 1986; crystalline metal aluminophosphates (MeAPO where "Me" is at least one of Mg, Mn, Co and Zn) are disclosed in U.S. Pat. No. 4,567,029, issued Jan. 28, 1986; crystalline ferroaluminophosphates (FeAPO) are disclosed in U.S. Pat. No. 4,554,143, issued Nov. 19, 1985; titanium aluminophosphates (TAPO) are disclosed in U.S. Pat. No. 4,500,651, issued Feb. 19, 1985; certain non-zeolitic molecular sieves ("ELAPO") are disclosed in EPC patent application Nos. 85104386.9 (Publication No. 0158976, published Oct. 13, 1985) and 85104388.5 (Publication No. 158349, published Oct. 16, 1985); and ELAPSO molecular sieves are disclosed in copending U.S. Ser. No. 600,312, filed Apr. 13, 1984 (EPC Publication No. 0159624, published Oct. 30, 1985). The aforementioned applications and patents are incorporated herein by reference thereto. The nomenclature employed herein to refer to the members of the aforementioned NZMS is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMS set forth hereinafter the mole fraction of the NZMS are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC Publication No. 0159,624, published Oct. 30, 1985, incorporated herein by reference) as crystalline molecular sieves having three-dimensional microporous framework structures of $ELO_2$, $AlO_2$, $PO_2$, $SiO_2$ oxide units and having an empirical chemical composition on an anhydrous basis expressed by the formula:

$$mR:(EL_wAl_xP_ySi_z)O_2$$

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a three dimensional oxide framework, "EL" being characterized as an element having a mean "T—O" distance in tetrahedral oxide structures between about 1.51 Angstroms and about 2.06 Angstroms, "EL" having a cation electronegativity between about 125 Kcal/g-atom to about 310 Kcal/gm-atom and "EL" being capable of forming stable M—O—P, M—O—Al or M—O—M bonds in crystalline three dimensional oxide structures having a "M—O" bond dissociation energy greater than about 59 kcal/g-atom at 298° K.; and "w", "x", "y" and "z" represent the mole fractions of "EL", aluminum, phosphorus and silicon, respectively, present as framework oxides, said mole fractions being within the limiting compositional values or points as follows:

| Point | Mole Fraction | | |
|-------|------|------|---------|
|       | x    | y    | (z + w) |
| A | 0.60 | 0.39-(0.01p) | 0.01(p + 1) |
| B | 0.39-(0.01p) | 0.60 | 0.01(p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "El" in the $(EL_wAl_xP_ySi_z)O_2$ constituent.

The "ELAPSO" molecular sieves are also described as crystalline molecular sieves having three-dimensional microporous framework structures of $ELO_2$, $AlO_2$,- $SiO_2$ and $PO_2$ tetrahedral oxide units and having an empirical chemical composition on an anhydrous basis expressed by the formula:

$$mR:(EL_wAl_xP_ySi_z)O_2$$

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides, said mole fractions being within the limiting compositional values or points as follows:

| Point | Mole Fraction | | |
|-------|------|------|---------|
|       | x    | y    | (z + w) |
| a | 0.60 | 0.39-(0.01)p | 0.01(p + 1) |
| b | 0.39-(0.01p) | 0.60 | 0.01(p + 1) |
| c | 0.10.55 | 0.35 | |
| d | 0.55 | 0.10 | 0.35 | where "p" is as above defined.

The "ELAPSO" molecular sieves include numerous species which are intended herein to be within the scope of the term "non-zeolitic molecular sieves" such being disclosed in the following copending and commonly assigned applications, incorporated herein by reference thereto:

| U.S. Serial No. | Filed | NZMS |
|---|---|---|
| 599,808(A) | April 13, 1984 | AsAPSO |
| U.S. Serial No. | Filed | NZMS |
| 845,484(CIP) | March 31, 1986 | AsAPSO |
| 600,177(A) | April 13, 1984 | BAPSO |
| 845,255(CIP) | March 28, 1986 | BAPSO |
| 600,176(A) | April 13, 1984 | BeAPSO |
| 841,752(CIP) | March 20, 1986 | BeAPSO |
| 599,830(A) | April 13, 1984 | CAPSO |
| 852,174(CIP) | April 15, 1986 | CAPSO |
| 599,925(A) | April 13, 1984 | GaAPSO |
| 845,985(CIP) | March 31, 1986 | GaAPSO |
| 599,971(A) | April 13, 1984 | GeAPSO |
| 852,175(CIP) | April 15, 1986 | GeAPSO |
| 599,952(A) | April 13, 1984 | LiAPSO |
| 847,227(CIP) | April 2, 1986 | LiAPSO |
| 600,179 (now U.S. Pat. No. 4,684,617 issued August 4, 1987) | April 13, 1984 | TiAPSO |
| 049,274(C) | May 13, 1987 | TiAPSO |
| 600,180 | April 13, 1984 | MgAPSO |
| 600,175 (now U.S. Pat. No. 4,686,092 issued August 11, 1987) | April 13, 1984 | MnAPSO |
| 600,174 | April 13, 1984 | CoAPSO |
| 600,170 | April 13, 1984 | ZnAPSO |
| 600,173 (now U.S. Pat. No. 4,683,217 issued July 28, 1987) | April 13, 1984 | FeAPSO |
| 600,168(A) | April 13, 1984 | QuinAPSO |
| 063,791(C) | June 22, 1987 | QuinAPSO |
| 600,181 | April 13, 1984 | QuinAPSO |
| 600,182 | April 13, 1984 | CoMnMgAPSO |

-continued

| | | |
|---|---|---|
| 057,648(C) | June 9, 1987 | CoMnMgAPSO |
| 600,183 | April 13, 1984 | SenAPSO |

The disclosures of the patents listed in the foregoing table are herein incorporated by reference.

TiAPSO MOLECULAR SIEVES

As already mentioned, the TiAPSO molecular sieves are described in U.S. Pat. No. 4,684,617 (incorporated herein by reference); these TiAPSO molecular sieves are also described in U.S. Ser. No. 049,274, filed May 13, 1987.

MgAPSO MOLECULAR SIEVES

The MgAPSO molecular sieves of U.S. Ser. No. 600,180, filed Apr. 13, 1984 have three-dimensional microporous framework structures of $MgO_2^{-2}$, $AlO_2^{-}$, $PO_2^{+}$ and $SiO_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

$$aR:(Mg_wAl_xP_ySi_z)O_2:bH_2O$$

wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:

(a) Alipro: aluminum isopropoxide;
(b) CATAPAL: Trademark of Condea for hydrated pseudoboehmite;
(c) LUDOX-LS: Trademark of DuPont for an aqueous solution of 30 weight percent $SiO_2$ and 0.1 weight percent $Na_2O$;
(d) Mg(Ac)$_2$: magnesium acetate tetrahydrate, $Mg(C_2H_3O_2)_2 \cdot 4H_2O$;
(e) $H_3PO_4$: 85 weight percent aqueous phosphoric acid in water;
(f) TBAOH: tetrabutylammonium hydroxide (40 wt. % in water);
(g) Pr$_2$NH: di-n-propylamine;
(h) Pr$_3$NH: tri-n-propylamine;
(i) Quin: Quinuclidine;
(j) MQuin: Methyl Quinuclidine hydroxide, (17.9%) in water);
(k) C-hex: cyclohexylamine;

(l) TEAOH: tetraethylammonium hydroxide (40 wt. % in water);
(m) DEEA: Diethylethanolamine;
(n) i-Pr$_2$NH: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

$$eR:fMgO:hAl_2O_3:iP_2O_5:gSiO_2:jH_2O$$

wherein e, f, g, h, i and j represent the moles of template R, magnesium (expressed as the oxide), SiO$_2$, Al$_2$O$_3$, P$_2$O$_5$ (H$_3$PO$_4$ expressed as P$_2$O$_5$) and H$_2$O, respectively.

The reaction mixtures may be prepared by the following representative procedures, designated hereinafter as Methods A, B and C.

Method A

The reaction mixture is prepared by mixing the ground aluminum source (alipro or CATAPAL) with the H$_3$PO$_4$ and water on a gradual basis with occasional cooling with an ice bath. The resulting mixture is blended until a homogeneous mixture is observed. When the aluminum source is CATAPAL the water and H$_3$PO$_4$ are first mixed with the CATAPAL added thereto. The magnesium acetate is dissolved in a portion of the water and is then added followed by addition of the LUDOX-LS. The combined mixture is blended until a homogeneous mixture is observed. The organic templating agent is added to this mixture and blended until a homogeneous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out under autogenous pressure. The products are removed from the reaction vessel, cooled and evaluated as set forth hereinafter.

Method B

When method B is employed the organic templating agent is di-n-propylamine. The aluminum source, silicon source and one-half of the water are first mixed and blended until a homogeneous mixture is observed. A second solution was prepared by mixing the remaining water, the H$_3$PO$_4$ and the magnesium acetate. This solution is then added to the above mixture. The magnesium acetate and H$_3$PO$_4$ solution is then added to the above mixture and blended until a homogeneous mixture is observed. The organic templating agent(s) is/are then added and the resulting reaction mixture digested and product recovered as in Method A.

Method C

Method C is carried out by mixing aluminum isopropoxide, LUDOX LS and water in a blender or by mixing water and aluminum iso-propoxide in a blender followed by addition of the LUDOX LS. H$_3$PO$_4$ and magnesium acetate are then added to the resulting mixture. The organic templating agent is then added to the resulting mixture and digested and product recovered as in Method A.

MnAPSO MOLECULAR SIEVES

As already mentioned, the MnAPSO molecular sieves are described in U.S. Pat. No. 4,686,092 issued Aug. 11, 1987 (incorporated herein by reference).

CoAPSO MOLECULAR SIEVES

The CoAPSO molecular sieves of U.S. Ser. No. 600,174, filed Apr. 13, 1984 have three-dimensional microporous framework structures of CoO$_2^{-2}$, AlO$_2^-$, PO$_2^+$ and SiO$_2$ tetrahedral units and have an empirical chemical composition on an anhydrous basis expressed by the formula:

$$mR:(Co_2Al_xP_ySi_z)O_2$$

wherein "R" represents at least one organic templating agent present in the intracrystalline pore system; "m" represents the molar amount of "R" present per mole of (Co$_w$Al$_x$P$_y$Si$_z$)O$_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure-directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$$aR:(Co_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|-------|------|------|---------|
|       | x    | y    | (z + w) |
| F     | 0.60 | 0.38 | 0.02    |
| G     | 0.38 | 0.60 | 0.02    |
| H     | 0.01 | 0.60 | 0.39    |
| I     | 0.01 | 0.01 | 0.98    |
| J     | 0.60 | 0.01 | 0.39    |

In the foregoing expression of the reaction composition, the reactants are normalized with respect to the total of "w", "x", "y" and "z" such that (w+x+y+z) = 1.00 mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepare CoAPSOs include:
(a) Alipro: aluminum isopropoxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) Co(Ac)$_2$: cobalt acetate, Co(C$_2$H$_3$O$_2$)$_2$"4H$_2$O;
(e) CoSO$_4$: cobalt sulfate, (CoSO$_4$"7H$_2$O);
(f) H$_3$PO$_4$: 85 weight percent phosphoric acid in water;
(g) TBAOH: tetrabutylammonium hydroxide (25 wt % in methanol);
(h) Pr$_2$NH: di-n-propylamine, (C$_3$H$_7$)$_2$NH;
(i) Pr$_3$N: tri-n-propylamine, (C$_3$H$_7$)$_3$N;
(j) Quin: Quinuclidine (C$_7$H$_{13}$N);
(k) MQuin: Methyl Quinuclidine hydroxide, (C$_7$H$_{13}$NCH$_3$OH):
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

$$eR:fCoO:hAl_2O_3:iP_2O_5:gSiO_2:jH_2O$$

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively.

The reaction mixtures are prepared by forming a starting reaction mixture comprising the $H_3PO_4$ and one half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., Co(Ac)$_2$, Co(SO$_4$) or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units having an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|-------|------|------|---------|
|       | x    | y    | (z + w) |
| A     | 0.60 | 0.38 | 0.02    |
| B     | 0.38 | 0.60 | 0.02    |
| C     | 0.01 | 0.60 | 0.39    |
| D     | 0.01 | 0.01 | 0.98    |
| E     | 0.60 | 0.01 | 0.39    |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

In synthesizing the ZnAPSO compositions, it is preferred to employ a reaction mixture composition expressed in terms of the molar ratios as follows:

$$aR:(Zn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.06 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing zinc, aluminum, phosphorus and silicon as framework tetrahedral oxide units are prepared as follows:

Preparative Reagents

ZnAPSO compositions are typically prepared using numerous reagents. Reagents which may be employed to prepare ZnAPSOs include:

(a) Alipro: aluminum isopropoxide;
(b) LUDOX-LS: LUDOX-LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite;
(d) $H_3PO_4$: 85 weight percent aqueous phosphoric acid;
(e) ZnAc: Zinc Acetate, $Zn(C_2H_3O_2)_2 \cdot 4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH \cdot 5H_2O$;
(i) TPAOH: 40 weight percent aqueous solution of tetrapropylammonium hydroxide, $(C_3H_7)_4NOH$;
(j) $Pr_2NH$: Di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

Preparative Procedure

ZnAPSO compositions are typically prepared by forming reaction mixtures having a molar composition expressed as:

$$eR:fZnO:gAl_2O_3:hP_2O_5:iSiO_2:jH_2O$$

wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively.

The reaction mixtures are generally prepared by forming a starting reaction mixture comprising the $H_3PO_4$ and a portion of the water. This mixture is stirred and the aluminum source added. The resulting mixture is blended until a homogeneous mixture is observed. The LUDOX LS is then added to the resulting mixture and the new mixture blended until a homogeneous mixture is observed. The zinc source (zinc acetate) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at an effective temperature for an effective time. Digestions are typically carried out under autogenous pressure. The products are removed from the reaction vessel and cooled.

FeAPSO MOLECULAR SIEVES

As already mentioned, the FeAPSO molecular sieves are described in U.S. Pat. No. 4,683,217 (incorporated herein by reference).

QUINARY MOLECULAR SIEVES

The QuinAPSO quinary molecular sieves of U.S. Ser. Nos. 600,168 and 600,181, both filed Apr. 13, 1984, have three-dimensional microporous framework structures of $MO_2^n$, $AlO_2^-$, $PO_2^+$ and $SiO_2$ tetrahedral units, where "n" is $-3$, $-2$, $-1$, 0 or $+1$, and have an empirical chemical composition on an anhydrous basis expressed by the formula:

$$mR:(M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$ and has a value of from zero (0) to about 0.3; M represents at least two elements selected from the group consisting of arsenic, beryllium, boron, chromium, cobalt, gallium, germanium, iron, lithium, magnesium, manganese, titanium, vanadium and zinc; and "w", "x", "y" and "z" represent the mole fractions of M, aluminum, phosphorus and silicon, respectively, present as tetrahedral oxides. Preferably, M represents the combination of cobalt and manganese. The mole fractions "w", "x", "y", and "z" are generally defined as being within the limiting compositional values or points as follows:

| Point | Mole Fraction | | |
|-------|------|------|---------|
|       | x    | y    | (z + w) |
| A     | 0.60 | 0.37 | 0.03    |
| B     | 0.37 | 0.60 | 0.03    |
| C     | 0.01 | 0.60 | 0.39    |
| D     | 0.01 | 0.01 | 0.98    |
| E     | 0.60 | 0.01 | 0.39    |

Preferably the mole fractions w, x, y and z will fall within the limiting compositional values or points as follows:

| Point | Mole Fraction | | |
|-------|------|------|---------|
|       | x    | y    | (z + w) |
| a     | 0.60 | 0.37 | 0.03    |
| b     | 0.37 | 0.60 | 0.03    |
| c     | 0.01 | 0.60 | 0.39    |
| d     | 0.01 | 0.39 | 0.60    |
| e     | 0.39 | 0.01 | 0.60    |
| f     | 0.60 | 0.01 | 0.39    |

QuinAPSO compositions are generally synthesized by hydrothermal crystallization from a reaction mixture containing reactive sources of the elements M, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the QuinAPSO product are obtained, usually over a period of from several hours to several weeks. Typical effective crystallization times are from about 2 hours to 30 days with from about 4 hours to about 20 days being generally employed to obtain QuinAPSO products. The product is recovered by any convenient method such as centrifugation or filtration.

In synthesizing the QuinAPSO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of elements M, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|-------|------|------|---------|
|       | x    | y    | (z + w) |
| F     | 0.60 | 0.37 | 0.03    |
| G     | 0.37 | 0.60 | 0.03    |
| H     | 0.01 | 0.60 | 0.39    |
| I     | 0.01 | 0.01 | 0.98    |
| J     | 0.60 | 0.01 | 0.39    |

In the foregoing expression of the reaction composition, the reactants are normalized with respect to the total of "w", "x", "y" and "z" such that (w+x+y+z)=1.00 mole. QuinAPSO compositions were prepared using numerous reagents; the appropriate sources of the various elements M are the same as those used in the preparation of the various APO and APSO molecular sieves containing the same elements, as described in detail above and below.

Reagents which may be employed to prepare QuinAPSOs include:

(a) Alipro: aluminum isopropoxide;
(b) LUDOX-LS: LUDOX-LS is the tradename of DuPont for an aqueous solution of 30 weight percent $SiO_2$ and 0.1 weight percent of $Na_2O$;
(c) $H_3PO_4$: 85 weight percent phosphoric acid;
(d) MnAc: Manganese acetate, $Mn(C_2H_3O_2)_2 \cdot 4H_2O$ (for QuinAPSOs containing manganese);
(e) CoAc: Cobalt Acetate, $Co(C_2H_3O_2)_2 \cdot 4H_2O$ (for QuinAPSOs containing cobalt);
(f) TEAOH: 40 weight percent aqueous solution of tetraethylammonium hydroxide; and
(g) $Pr_2NH$: di-n-propylamine, $(C_3H_7)_2NH$.

Preparative Procedures

QuinAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate (or a appropriate source of another element M) and one half of the remaining water. A third mixture is prepared using cobalt acetate (or a appropriate source of another element M) and one half of the remaining water. The three mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at an effective temperature for an effective time. Digestions are typically carried out under autogeneous pressure.

CoMnMgAPSO MOLECULAR SIEVES

The CoMnMgAPSO senary molecular sieves of U.S. Ser. No. 600,182, filed Apr. 13, 1984, and of U.S. Ser. No. 057,648 filed June 9, 1987, have three-dimensional microporous framework structures of $CoO_2^{-2}$, $MnO_2^{-2}$, $MgO_2^{-2}$, $AlO_2$, $PO_2^+$ and $SiO_2$ tetrahedral oxide units having an empirical chemical composition on an anhydrous basis expressed by the formula:

$$mR:(Co_tMn_uMg_vAl_xP_ySi_z)O_2$$

wherein "R" represents at least one organic templating agent present in the intracrystalline pore system; "m" represents the molar amount of "R" present per mole of $(Co_tMn_uMg_vAl_xP_ySi_z)O_2$ and has a value of from zero (0) to about 0.3; "t", "u", "v", "x", "y" and "z" represent the mole fractions of cobalt, manganese, magnesium, aluminum, phosphorus and silicon, respectively, present as tetrahedral oxides and each has a value of at least 0.01. The mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure-directing agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

$$aR:(Co_tMn_uMg_vAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each ha a value of at least 0.01.

In a preferred embodiment the reaction mixture is selected such that the mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that (t+u+v+x+y+z)=1.00 mole. Molecular sieves containing cobalt, manganese, magnesium, aluminum, phosphorus and silicon as framework tetrahedral oxide units are prepared as follows:

Preparative Reagents

CoMnMgAPSO compositions may be prepared by using numerous reagents. Reagents which may be employed to prepare CoMnMgAPSOs include:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$:aqueous solution which is 85 weight percent phosphoric acid;
(d) MnAc: Manganese acetate, $Mn(C_2H_3O_2)_2 \cdot 4H_2O$;
(e) CoAc: Cobalt Acetate, $Co(C_2H_3O_2)_2 \cdot 4H_2O$;
(f) MgAc: Magnesium Acetate $Mg(C_2H_3O_2) \cdot 4H_2O$;
(g) TEAOH: 40 weight percent aqueous solution of tetraethylammonium hydroxide; and
(h) $Pr_2NH$: di-n-propylamine, $(C_3H_7)_2NH$.

Preparative Procedures

CoMnMgAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate using one third of the remainder of the water for each mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at a temperature for a time. Digestions are typically carried out under autogenous pressure.

SenAPSO MOLECULAR SIEVES

The SenAPSO molecular sieves of U.S. Ser. No. 600,183, filed Apr. 13, 1984 have three-dimensional microporous framework structures of $MO_2{}^n$, $AlO_2{}^-$, $PO_2{}^+$ and $SiO_2$ tetrahedral oxide units, where "n" is $-3$, $-2$, $-1$, 0 or $+1$, and have an empirical chemical composition on an anhydrous basis expressed by the formula:

$$mR:(M_wAl_xP_ySi_z)O_2$$

wherein "R" represents at leas one organic templating agent present in the intracrystalline pore system; "m" represents the molar amount of "R" present per mole of $(M_wAl_xP_ySi_z)O_2$, and has a value of from zero to about 0.3; "M" represent three elements selected from the group consisting of arsenic, beryllium, boron, chromium, cobalt, gallium, germanium, iron, lithium, magnesium, manganese, titanium, vanadium and zinc; "n" may have the aforementioned values depending upon the oxidation state of "M"; and "w", "x", "y" and "z" represent the mole fractions of elements "M", aluminum, phosphorus and silicon, respectively, present as tetrahedral oxides. The mole fractions "w", "x", "y" and "z" are generally defined as being within the limiting compositional values or points as follows, wherein "w" denotes the combined mole fractions of the three elements "M" such that "w"="$w_1$"+"$w_2$"+"$w_3$" and each element "M" has a mole fraction of at least 0.01:

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the SenAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.60 | 0.36 | 0.04 |
| b | 0.36 | 0.60 | 0.04 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

SenAPSO compositions are generally synthesized by hydrothermal crystallization from a reaction mixture containing reactive sources of elements "M", aluminum, phosphorus and silicon, and preferably an organic templating, i.e., structure-directing, agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the SenAPSO product are obtained, usually over a period of from several hours to several weeks. Typical crystallization times are from about 2 hours to about 30 days with from about 4 hours to about 20 days generally being employed to obtain SenAPSO products. The product is recovered by any convenient method such as centrifugation or filtration.

In synthesizing the SenAPSO compositions, it is preferred to employ a reaction mixture composition expressed in terms of the molar ratios as follows:

$$aR:(M_wAl_xP_ySi_z)O_2 :bH_2O$$

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "w", "x", "y", and "z" represent the mole fractions of elements "M", aluminum, phosphorus and silicon, respectively, and each has a value of at least 0.01, with the proviso that each "M" is present in a mole fraction of at least 0.01.

In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. The SenAPSO molecular sieves are prepared by preparative techniques, and using sources of the elements "M" similar to those described for the other APSO molecular sieves described above and below.

AsAPSO MOLECULAR SIEVES

The AsAPSO molecular sieves of U.S. Ser. No. 599,808, filed Apr. 13, 1984, and U.S. Ser. No. 845,484 filed Mar. 31, 1986 have a framework structure of $AsO_2{}^n$, $AlO_2{}^-$, $PO_2{}^+$ and $SiO_2$ tetrahedral units having an empirical chemical composition on an anhydrous basis expressed by the formula:

$$mR:(As_wAl_xP_ySi_z)O_2$$

wherein "R" represents at least one organic templating agent present in the intracrystalline pore system; "m" represents the molar amount of "R" present per mole of $(As_wAl_xP_ySi_z)O_2$ and has a value of zero to about 0.3, but is preferably greater than 0.15; and "w", "x", "y" and "z" represent the mole fractions of the elements arsenic, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the AsAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the AsAPSO molecular sieves, the values of w, x, y and z are as follows:

| Point | Mole Fraction | | |
|---|---|---|---|
| | x | y | (z + w) |
| g | 0.50 | 0.40 | 0.10 |
| h | 0.42 | 0.48 | 0.10 |
| i | 0.38 | 0.48 | 0.14 |
| j | 0.38 | 0.37 | 0.25 |
| k | 0.45 | 0.30 | 0.25 |
| l | 0.50 | 0.30 | 0.20 |

AsAPSO compositions are generally synthesized by hydrothermal crystallization from a reaction mixture containing reactive sources of arsenic, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPSO product are obtained, usually a period of from several hours to several weeks. Typical effective times of from 2 hours to about 30 days, generally from about 12 hours to about 10 days, have been observed. The product is recovered by any convenient method such as centrifugation or filtration.

In synthesizing the AsAPSO compositions, it is preferred to employ a reaction mixture composition expressed in terms of the molar ratios as follows:

$$aR:(As_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 60; and "w", "x", "y" and "z" represent the mole fractions of arsenic, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 1 to about 2 total moles of silicon and arsenic, and from about 1 to about 2 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing arsenic, aluminum, phosphorus and silicon as framework tetrahedral oxide units are prepared as follows:

Preparative Reagents

AsAPSO compositions may be prepared by using numerous reagents. Reagents which may be employed to prepare AsAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) $As_2O_5$, arsenic (V) oxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

AsAPSOs may be prepared by forming a starting reaction mixture by dissolving the arsenic (V) oxide and the H$_3$PO$_4$ in at least part of the water. To this solution the aluminum isopropoxide or CATAPAL is added. This mixture is then blended until a homogeneous mixture is observed. To this mixture the templating agent and then the silica is added and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BAPSO MOLECULAR SIEVES

The BAPSO molecular sieves of U.S. Ser. No. 600,177, filed Apr. 13, 1984, and U.S. Ser. No. 845,255 filed Mar. 28, 1986 have a framework structure of BO$_2^-$, AlO$_2^-$, PO$_2^+$ and SiO$_2$ tetrahedral units having an empirical chemical composition on an anhydrous basis expressed by the formula:

$$mR:(B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3, but is preferably not greater than 0.15; and "w", "x", "y" and "z" represent the mole fractions of the elements boron, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the BAPSO molecular sieves, the values of w, x, y and z are as follows:

| Point | Mole Fraction | | |
|---|---|---|---|
| | x | y | (z + w) |
| g | 0.51 | 0.42 | 0.07 |
| h | 0.45 | 0.48 | 0.07 |
| i | 0.33 | 0.48 | 0.19 |
| j | 0.33 | 0.38 | 0.29 |
| k | 0.36 | 0.35 | 0.29 |
| l | 0.51 | 0.35 | 0.14 |

BAPSO compositions are generally synthesized by hydrothermal crystallization from a reaction mixture containing reactive sources of boron, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BAPSO product are obtained, usually a period of from several hours to several weeks. Typical effective times of from 2 hours to about 30 days, generally from about 4 hours to about 20 days, have been observed. The product is recovered by any convenient method such as centrifugation or filtration.

In synthesizing the BAPSO compositions, it is preferred to employ a reaction mixture composition expressed in terms of the molar ratios as follows:

$$aR:(B_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of boron, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 1.0 to about 2 total moles of silicon and boron, and from about 0.75 to about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing boron, aluminum, phosphorus and silicon as framework tetrahedral oxide units are prepared as follows:

Preparative Reagents

BAPSO compositions may be prepared by using numerous reagents. Reagents which may be employed to prepare BAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) $H_3BO_3$, boric acid, and trialkyl borates;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BAPSOs may be prepared by forming a starting reaction mixture by dissolving aluminum isopropoxide in an alcohol such as isopropanol, adding the $H_3PO_4$ and recovering the solid which precipitates. This solid is then added to water, and trialkylborate (for example trimethyl borate) added, followed by silica and the templating agent. This mixture is then blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPSO MOLECULAR SIEVES

The BeAPSO molecular sieves of U.S. Ser. No. 600,176, filed Apr. 13, 1984, and U.S. Ser. No. 841,752 filed Mar. 20, 1986 have a framework structure of $BeO_2^{-2}$, $AlO_2^-$, $PO_2^+$ and $SiO_2$ tetrahedral units having an empirical chemical composition on an anhydrous basis expressed by the formula:

$$mR:(Be_wAl_xP_ySi_z)O_2$$

wherein "R" represents at least one organic templating agent present in the intracrystalline pore system; "m" represents the molar amount of "R" present per mole of $(Be_wAl_xP_ySi_z)O_2$ and has a value of zero to about 0.3, but is preferably not greater than 0.15; and "w", "x", "y" and "z" represent the mole fractions of the elements beryllium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BeAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

BeAPSO compositions are generally synthesized by hydrothermal crystallization from a reaction mixture containing reactive sources of beryllium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the BeAPSO product are obtained, usually a period of from several hours to several weeks. Typical effective times of from 2 hours to about 30 days, generally from about 4 hours to about 20 days, have been observed, with from 1 to 10 days being preferred. The product is recovered by any convenient method such as centrifugation or filtration.

In synthesizing the BeAPSO compositions, it is preferred to employ a reaction mixture composition expressed in terms of the molar ratios as follows:

$$aR:(Be_wAl_xP_ySi_z)O_2:bH_2O$$

wherein "R" is an organic templating agent, "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 to about 300, most preferably not greater than about 20; and "w", "x", "y" and "z" represent the mole fractions of beryllium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |

-continued

| | Mole Fraction | | |
|---|---|---|---|
| Point | x | y | (z + w) |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing beryllium, aluminum, phosphorus and silicon as framework tetrahedral oxide units are prepare as follows:

Preparative Reagents

BeAPSO compositions may be prepared by using numerous reagents. Reagents which may be employed to prepare BeAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) beryllium sulfate, $BeSO_4$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BeAPSOs may be prepared by forming a starting solution by mixing $H_3PO_4$ in at least part of the water. To this solution is added beryllium sulfate (or another beryllium salt) and the resultant mixture stirred until a homogeneous solution is obtained. To this solution may be added successively the aluminum oxide, the silica and the templating agent, with the mixture being stirred between each addition until it is homogeneous. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

CAPSO MOLECULAR SIEVES

The CAPSO molecular sieves of U.S. Ser. No. 599,830, filed Apr. 13, 1984, and U.S. Ser. No. 852,174 filed Apr. 15, 1986 have a framework structure of $CrO_2{}^n$, $AlO_2{}^-$, $PO_2{}^+$ and $SiO_2$ tetrahedral units (where "n" is −1, 0 or +1) having an empirical chemical composition on an anhydrous basis expressed by the formula:

$$mR:(Cr_wAl_xP_ySi_z)O_2$$

wherein "R" represents at least one organic templating agent present in the intracrystalline pore system; "m" represents the molar amount of "R" present per mole of $(Cr_wAl_xP_ySi_z)O_2$ and has a value of zero to about 0.3, but is preferably not greater than 0.15; and "w", "x", "y" and "z" represent the mole fractions of the elements chromium, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CAPSO molecular sieves, the values of w, x, y and z are as follows:

| | Mole Fraction | | |
|---|---|---|---|
| Point | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the CAPSO molecular sieves, the values of x and y in the above formula are each within the range of about 0.4 to 0.5 and (z+w) is in the range of about 0.02 to 0.15.

Since the exact nature of the CAPSO molecular sieves is not clearly understood at present, although all are believed to contain $CrO_2$ tetrahedral in the three-dimensional microporous crystal framework structure, it is advantageous to characterize the CAPSO molecular sieves by means of their chemical composition. This is due to the low level of chromium present in certain of the CAPSO molecular sieves prepared to date which makes it difficult to ascertain the exact nature of the interaction between chromium, aluminum, phosphorus and silicon. As a result, although it is believed that $CrO_2$ tetrahedral are substituted isomorphously for $AlO_2$, $PO_2$ or $SiO_2$ tetrahedral, it is appropriate to characterize certain CAPSO compositions by reference to their chemical composition in terms of the mole ratios of oxides.

CAPSO compositions are generally synthesized by hydrothermal crystallization from a reaction mixture containing reactive sources of chromium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the CAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the CAPSO compositions, it is preferred to employ a reaction mixture composition expressed in terms of the molar ratios as follows:

$$aR:(Cr_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of chromium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.3 to about 0.5 total moles of silicon and chromium, and from about 0.75 to about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing chromium, aluminum, phosphorus and silicon as framework tetrahedral oxide units are prepared as follows:

Preparative Reagents

CAPSO compositions may be prepared by using numerous reagents. Reagents which may be employed to prepare CAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) chromium acetate, and chromium acetate hydroxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

CAPSOs may be prepared by forming a starting solution by dissolving $H_3PO_4$ in at least part of the water. To this solution the aluminum isopropoxide is added. This mixture is then blended until a homogeneous mixture is observed. To this mixture the silica, the chromium acetate or chromium acetate hydroxide and the templating agent are successively added and at each step the resulting mixture is blended until a homogeneous mixture is observed.

Alternatively, the water and aluminum isopropoxide may first be mixed, and then the silica, the chromium acetate or chromium acetate hydroxide, the phosphoric acid and the templating agent added, and again at each step the resulting mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPSO MOLECULAR SIEVES

The GaAPSO molecular sieves of U.S. Ser. No. 599,925, filed Apr. 13, 1984, and U.S. Ser. No. 845,985 filed Mar. 31, 1986 have a framework structure of $GaO_2^-$, $AlO_2^-$, $PO_2^+$ and $SiO_2$ tetrahedral units having an empirical chemical composition on an anhydrous basis expressed by the formula:

$$mR:(Ga_wAl_xP_ySi_z)O_2$$

wherein "R" represents at least one organic templating agent present in the intracrystalline pore system; "m" represents the molar amount of "R" present per mole of $(Ga_wAl_xP_ySi_z)O_2$ and has a value of zero to about 0.3, but is preferably not greater than 0.2; and "w", "x", "y" and "z" represent the mole fractions of the elements gallium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the GaAPSO molecular sieves, the values of w, x, y and z are as follows:

| | Mole Fraction | | |
|---|---|---|---|
| Point | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GaAPSO molecular sieves, the values of w, x, y and z are as follows:

| | Mole Fraction | | |
|---|---|---|---|
| Point | x | y | (z + w) |
| g | 0.45 | 0.40 | 0.15 |
| h | 0.33 | 0.52 | 0.15 |
| i | 0.20 | 0.52 | 0.28 |
| j | 0.20 | 0.45 | 0.35 |
| k | 0.36 | 0.29 | 0.35 |
| l | 0.45 | 0.29 | 0.26 |

GaAPSO compositions are generally synthesized by hydrothermal crystallization from a reaction mixture containing reactive sources of gallium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPSO product are obtained, usually a period of from several hours to several weeks. Typical effective times of from 2 hours to about 30 days, generally from about 4 hours to about 20 days, and preferably about 2 to about 15 days, have been observed. The product is recovered by any convenient method such as centrifugation or filtration.

In synthesizing the GaAPSO compositions, it is preferred to employ a reaction mixture composition expressed in terms of the molar ratios as follows:

$aR:(Ga_wAl_xP_ySi_z)O_2:bH_2O$ wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 20; and "w", "x", "y" and "z" represent the mole fractions of gallium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |

| | Mole Fraction | | |
|---|---|---|---|
| Point | x | y | (z + w) |
| I | 0.01 | 0.01 | 0.98 |
| J | 0.60 | 0.01 | 0.39 |

Especially preferred reaction mixtures are those containing from about 0.5 to about 1.0 total moles of silicon and gallium, and from about 0.75 about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing gallium, aluminum, phosphorus and silicon as framework tetrahedral oxide units are prepared as follows:

Preparative Reagents

GaAPSO compositions may be prepared by using numerous reagents. Reagents which may be employed to prepare GaAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) gallium hydroxide, or gallium sulfate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

GaAPSOs may be prepared by forming a starting solution by dissolving $H_3PO_4$ in at least part of the water. To this solution the aluminum hydroxide or isopropoxide is added. This mixture is then blended until a homogeneous mixture is observed. To this mixture is added a second solution prepared by adding silica to a solution containing the gallium hydroxide and the templating agent and then the combined mixture is blended until a homogeneous mixture is observed.

Alternatively, the templating agent may be added to the solution containing the phosphoric acid and water, and a solution of gallium sulfate in water added, followed by successive additions of silica and aluminum oxide and then the combined mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GeAPSO MOLECULAR SIEVES

The GeAPSO molecular sieves of U.S. Ser. No. 599,971, filed Apr. 13, 1984, and U.S. Ser. No. 852,175 filed Apr. 15, 1986 have a framework structure of $GeO_2$, $AlO_2^-$, $PO_2^+$ and $SiO_2$ tetrahedral units having an empirical chemical composition on an anhydrous basis expressed by the formula:

$$mR:(Ge_wAl_xP_ySi_z)O_2$$

wherein "R" represents at least one organic templating agent present in the intracrystalline pore system; "m" represents the molar amount of "R" present per mole of $(Ge_wAl_xP_ySi_z)O_2$ and has a value of zero to about 0.3, but is preferably not greater than 0.15; and "w", "x", "y" and "z" represent the mole fractions of the elements geranium, aluminum, phosphorus and silicon, respectively, present as tetrahedral oxides. The mole fractions "w", "x", "y" and "z" are generally defined as being within the limited compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |

| Point | Mole Fraction | | |
|---|---|---|---|
| | x | y | (z + w) |
| D | 0.01 | 0.01 | 0.98 |
| E | 0.60 | 0.01 | 0.39 |

In a preferred subclass of the GeAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GeAPSO molecular sieves, the values of w, x, y and z are as follows:

| Point | Mole Fraction | | |
|---|---|---|---|
| | x | y | (z + w) |
| g | 0.60 | 0.35 | 0.05 |
| h | 0.47 | 0.48 | 0.05 |
| i | 0.40 | 0.48 | 0.12 |
| j | 0.40 | 0.36 | 0.24 |
| k | 0.46 | 0.30 | 0.24 |
| l | 0.60 | 0.30 | 0.10 |

GeAPSO compositions are generally synthesized by hydrothermal crystallization from a reaction mixture containing reactive sources of geranium, silicon, aluminum and phosphorus, preferably an organic templating, i.e., structure-directing, agent, preferably a compound of an element of Group VA of the Periodic Table, and-/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GeAPSO product are obtained, usually a period of from several hours to several weeks. Typical effective times of from 2 hours to about 30 days, generally from about 4 hours to about 20 days, and preferably about 12 hours to about 7 days have been observed. The product is recovered by any convenient method such as centrifugation or filtration.

In synthesizing the GaAPSO compositions, it is preferred to employ a reaction mixture composition expressed in terms of the molar ratios as follows:

$$aR:(Ge_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and desirably not greater than about 10; and "w", "x", "y" and "z" represent the mole fractions of germanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.2 to about 0.3 total moles of silicon and germanium, and from about 0.75 about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing germanium, aluminum, phosphorus and silicon as framework tetrahedral oxide units are prepared as follows:

Preparative Reagents

GeAPSO compositions may be prepared by using numerous reagents. Reagents which may be employed to prepare GeAPSOs include:
(a) Alipro: aluminum isopropoxide;
(b) CATAPAL: Trademark of Condea Corporation for hydrated pseudoboehmite;

(c) LUDOX-LS: LUDOX-LS is the tradename of DuPont for an aqueous solution of 30 weight percent SiO$_2$ and 0.1 weight percent Na$_2$O;
(d) H$_3$PO$_4$: 85 weight percent aqueous phosphoric acid;
(e) germanium tetrachloride or germanium ethoxide;
(f) TEAOH: 40 weight percent aqueous solution of tetraethylammonium hydroxide;
(g) TBAOH: 40 weight percent aqueous solution of tetrabutylammonium hydroxide;
(h) Pr$_2$NH: di-n-propylamine, (C$_3$H$_7$)$_2$NH;
(i) Pr$_3$N: tri-n-propylamine, (C$_3$H$_7$)$_3$N;
(j) Quin: Quinuclidine, (C$_7$H$_{13}$N);
(k) MQuin: Methyl Quinuclidine hydroxide, (C$_7$H$_{13}$NCH$_3$OH);
(l) C-hex: cyclohexylamine;
(m) TMAOH: tetramethylammonium hydroxide;
(n) TPAOH: tetrapropylammnnium hydroxide; and
(o) DEEA: 2-diethylaminoethanol;
(p) Tetraalkylorthosilicates, such as tetraethylorthosilicate; and
(q) aluminum chlorhydrol.

Preparative Procedures

In some cases, it may be advantageous, when synthesizing the GeAPSO compositions, to first combine sources of germanium and aluminum, or of germanium, aluminum and silicon, to form a mixed germanium/aluminum or germanium/aluminum/silicon compound (this compound being typically a mixed oxide) and thereafter to combine this mixed compound with a source of phosphorus to form the final GeAPSO composition. Such mixed oxides may be prepared for example by hydrolyzing aqueous solutions containing germanium tetrachloride and aluminum chlorhydrol, or germanium ethoxide, tetraethylorthosilicate, and aluminum tri-sec-butoxide.

GeAPSOs may be prepared by forming a starting solution by dissolving H$_3$PO$_4$ in at least part of the water. To this solution the aluminum isopropoxide or CATAPAL is added. This mixture is then blended until a homogeneous mixture is observed. To this mixture is the templating agent and then a solution containing tetraethylorthosilicate and germanium ethoxide, and the resulting mixture blended until a homogeneous mixture is observed.

Alternatively, the phosphoric acid may first be mixed with the templating agent, and then a solution containing tetraethylorthosilicate and germanium ethoxide combined with the phosphoric acid/templating agent solution. Then the aluminum oxide is added and the resultant mixture blended until homogeneous.

In a third procedure, the phosphoric acid may first be mixed with the templating agent and water, and to the resultant solution is added the solid aluminum/silicon/germanium mixed oxide prepared as described above. The resultant mixture is then blended until homogeneous.

Whichever procedure is adopted, the final mixture is then placed in a lined (polytetrafluoro- ethylene) stainless steel pressure vessel and digested at a temperature (150° C. or 200° C.) for a time or placed in lined screw top bottles for digestion at 100° C. Digestions are typically carried out under autogenous pressure.

LiAPSO MOLECULAR SIEVES

The LiAPSO molecular sieves of U.S. Ser. No. 599,952, filed Apr. 13, 1984, and U.S. Ser. No. 847,227 filed Apr. 2, 1986 have a framework structure of Li-O$_2^{-3}$, AlO$_2^-$, PO$_2^+$ and SiO$_2$ tetrahedral units having an empirical chemical composition on an anhydrous basis expressed by the formula:

mR:(Li$_w$Al$_x$P$_y$Si$_z$)O$_2$ wherein "R" represents at least one organic templating agent present in the intracrystalline pore system; "m" represents the molar amount of "R" present per mole of (Li$_w$Al$_x$P$_y$Si$_z$)O$_2$ and has a value of zero to about 0.3, but is preferably not greater than 0.15; and "w", "x", "y" and "z" represent the mole fractions of the elements lithium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the LiAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the LiAPSO molecular sieves, the value of w+z is not greater than about 0.20.

Since the exact nature of the LiAPSO molecular sieves is not clearly understood at present, although all are believed to contain LiO$_2$ tetrahedra in the three-dimensional microporous crystal framework structure, it is advantageous to characterize the LiAPSO molecular sieves by means of their chemical composition. This is due to the low level of lithium present in certain of the LiAPSO molecular sieves prepared to date which makes it difficult to ascertain the exact nature of the interaction between lithium, aluminum, phosphorus and silicon. As a result, although it is believed that LiO$_2$ tetrahedra are substituted isomorphously for AlO$_2$, PO$_2$ or SiO$_2$ tetrahedra, it is appropriate to characterize certain LiAPSO compositions by reference to their chemical composition in terms of the mole ratios of oxides.

LiAPSO compositions are generally synthesized by hydrothermal crystallization from a reaction mixture containing reactive sources of lithium, silicon, aluminum and phosphorus, preferably an organic templating, i.e., structure-directing, agent, preferably a compound of an element of Group VA of the Periodic Table, and-/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the LiAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the LiAPSO compositions, it is preferred to employ a reaction mixture composition expressed in terms of the molar ratios as follows:

$$aR:(Li_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20, and most desirably not greater than about 10; and "w", "x", "y" and "z" represent the mole fractions of lithium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing lithium, aluminum, phosphorus and silicon as framework tetrahedral oxide units are prepared as follows:

Preparative Reagents

LiAPSO compositions may be prepared by using numerous reagents. Reagents which may be employed to prepare LiAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous-phosphoric acid;
(e) lithium orthophosphate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

LiAPSOs may be prepared by forming a starting reaction mixture mixing lithium phosphate and aluminum oxide, then adding the resultant mixture to the $H_3PO_4$. To the resultant mixture is added silica and the templating agent and the resulting mixture is blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

AlPO4 ALUMINOPHOSPHATE MOLECULAR SIEVES

As already mentioned, the AlPO4 aluminophosphate molecular sieves are described in U.S. Pat. No. 4,310,440 (incorporated herein by reference); these AlPO4 molecular sieves are also described in U.S. Ser. No. 880,559, filed June 30, 1986.

MeAPO MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029 (incorporated herein by reference).

FAPO MOLECULAR SIEVES

As already mentioned, ferroaluminphosphates (FAPO's) are disclosed in U.S. Pat. No. 4,554,143 (incorporated herein by reference).

TAPO MOLECULAR SIEVES

As already mentioned, TAPO molecular sieves are disclosed in U.S. Pat. No. 4,500,561 (incorporated herein by reference).

ELAPO MOLECULAR SIEVES

"ELAPO" molecular sieves are a class of crystalline molecular sieves in which at least one element capable of forming a three-dimensional microporous framework forms crystal framework structures of $AlO_2^-$, $PO_2^+$ and $MO_2^n$ tetrahedral oxide units wherein "$MO_2^n$" represents at least one different element (other than Al or P) present as tetrahedral oxide units "$MO_2^n$" with charge "n" where "n" may be $-3$, $-2$, $-1$, 0 or $+1$. The members of this novel class of molecular sieve compositions have crystal framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2$$

wherein "R" represents at leas one organic templating agent present in the intracrystalline pore system; "m" represents the molar amount of "R" present per mole of ($M_xAl_yP_z$)$O_2$; "M" represents at least one element capable of forming framework tetrahedral oxides; and "x", "y" and "z" represent the mole fraction of "M", aluminum and phosphorus, respectively, present as tetrahedral oxides. "M" is at least one different (i.e., not aluminum, phosphorus or oxygen) element such that the molecular sieves contain at least one framework tetrahedral unit in addition to $AlO_2^-$ and $PO_2^+$. "M" is at least one element selected from the group consisting of arsenic, beryllium, boron, cobalt, chromium, gallium, germanium, iron, lithium, magnesium, manganese, titanium and zinc, subject to certain restrictions on the combinations of elements as will appear from the discussions of individual groups of ELAPOs below. ELAPOs and their preparation are disclosed in European Patent Application Ser. No. 85104386.9, filed Apr. 11, 1985 (EPC Publication No. 0158976, published Oct. 13, 1985, incorporated herein by reference) and 85104388.5, filed Apr. 11, 1985 (EPC Publication No. 158349, published Oct. 16, 1985, incorporated herein by reference).

The "ELAPO" molecular sieves further include numerous species which are intended herein to be within the scope of the term "non-zeolitic molecular sieves" such being disclosed in the following copending and commonly assigned applications, incorporated herein by reference thereto [(A) following a serial number indicates that the application is abandoned, while (CIP) following a serial number indicates that the application is a continuation-in-part of the immediately preceding application, and (C) indicates that the application is a continuation of the immediately preceding application]:

| U.S. Ser. No. | Filed | NZMS |
|---|---|---|
| 600,166(A) | April 13, 1984 | AsAPO |
| 830,889(CIP) | Feb. 19, 1986 | AsAPO |
| 599,812(A) | April 13, 1984 | BAPO |
| 804,248(C)(A) | Dec. 4, 1985 | BAPO |
| 029,540(CIP) | March 24, 1987 | BAPO |
| 599,776(A) | April 13, 1984 | BeAPO |
| 835,293(CIP) | March 3, 1986 | BeAPO |
| 599,813(A) | April 13, 1984 | CAPO |
| 830,756(CIP) | Feb. 19, 1986 | CAPO |
| 599,771(A) | April 13, 1984 | GaAPO |
| 830,890(CIP) | Feb. 19, 1986 | GaAPO |
| 599,807(A) | April 13, 1984 | GeAPO |
| 841,753(CIP) | March 20, 1986 | GeAPO |
| 599,811(A) | April 13, 1984 | LiAPO |
| 834,921(CIP) | Feb. 28, 1986 | LiAPO |
| 600,171 | April 13, 1984 | FCAPO |
| (now U.S. Pat. No. 4,686,093 issued August 11, 1987) | | |
| 600,172(A) | April 13, 1984 | ElAPO (M comprises two different elements) |
| 846,088(CIP) | March 31, 1986 | |
| 599,824(A) | April 13, 1984 | FeTiAPO |
| 902,129(C) | September 2, 1986 | FeTiAPO |
| 599,810(A) | April 13, 1984 | XAPO |
| 902,020(C) | September 2, 1986 | XAPO |

The disclosure of the patent listed in the foregoing table is incorporated herein by reference.

The ELAPO molecular sieves are generally referred to herein by the acronym "ELAPO" to designate element(s) "M" in a framework of $AlO_2^-$, $PO_2^+$ and $MO_2^n$ tetrahedral oxide units. Actual class members will be identified by replacing the "EL" of the acronym with the elements present as $MO_2^n$ tetrahedral units. For example, "MgBeAPO" designates a molecular sieve comprised of $AlO_2^-$, $PO_2^+$, $MgO_2^{-2}$ and $BeO_2^{-2}$ tetrahedral units. To identify various structural species which make up each of the subgeneric classes, each species is assigned a number and is identified as "ELAPO-i" wherein "i" is an integer. The given species designation is not intended to denote a similarity in structure to any other species denominated by a similar identification system.

The ELAPO molecular sieves comprise at least one additional element capable of forming framework tetrahedral oxide units ($MO_2^n$) to form crystal framework structures with $AlO_2^-$ and $PO_2^+$ tetrahedral oxide units wherein "M" represents at least one element capable of forming tetrahedral units "$MO_2^n$" where "n" is $-3$, $-2$, $-1$, $0$ or $+1$ and is at least one element selected from the group consisting of arsenic, beryllium, boron, cobalt, chromium, gallium, germanium, iron, lithium, magnesium, manganese, titanium and zinc.

The ELAPO molecular sieves have crystalline three-dimensional microporous framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2;$$

wherein "R" represents at leas one organic templating agent present in the intracrystalline pore system; "m" represents the molar amount of "R" present per mole of ($M_xAl_yP_z$)$O_2$ and has a value of zero to about 0.3; "M" represents at least one element capable of forming framework tetrahedral oxides where "M" is at least one element selected from the group consisting of arsenic, beryllium, boron, cobalt, chromium, gallium, germanium, iron, lithium, magnesium, manganese, titanium and zinc.

The relative amounts of element(s) "M", aluminum and phosphorous are expressed by the empirical chemical formula (anhydrous):

$$mR:(M_xAl_yP_z)O_2$$

where "x", "y" and "z" represent mole fractions of said "M" aluminum and phosphorous. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$" etc. represent the individual mole fractions of elements $M_1$, $M_2$, $M_3$, and etc. for "M" as above defined. The values of "$x_1$", "$x_2$", "$x_3$", etc. are as defined for "x", hereinafter, where "$x_1$"+"$x_2$"+"$x_3$" ... ="x" and where $x_1$, $x_2$, $x_3$, etc. are each at least 0.01.

The ELAPO molecular sieves have crystalline three-dimensional microporous framework structures of $MO_2^n$, $AlO_2^-$ and $PO_2^+$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of ($M_xAl_yP_z$)$O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorous, respectively present as tetrahedral oxides; in general, said mole fractions "x", "y" and "z" are within the following values for "x", "y" and "z", although as will appear hereinbelow, the limits for "x", "y" and "z" may vary slightly with the nature of the element "M":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

Also, in general, in a preferred sub-class of the ELAPOs of this invention, the values of "x", "y" and "z" in the formula above are within the following values for "x", "y" and "z", although again the relevent limits may vary somewhat with the nature of the element "M", as set forth hereinbelow:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is in general preferred to employ a reaction mixture composition expressed in terms of the molar ratios as follows:

$aR:(M_xAl_yP_z)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2^n$, with $AlO_2^-$ and $PO_2^+$ tetrahedral units; "n" has a value of $-3$, $-2$, $-1$, 0 or $+1$; and "x", "y" and "z" represent the mole fractions of "M", aluminum and phosphorous, respectively; "y" and "z" each have a value of at least 0.01 and "x" has a value of at least 0.01 with each element "M" having a mole fraction of at least 0.01. In general, the mole fractions "x", "y" and "z" are preferably within the following values for "x", "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Further guidance concerning the preferred reaction mixtures for forming ELAPOs with various elements "M" will be given below.

In the foregoing expression of the reaction composition, the reactants are normalized with respect to a total of $(M+Al+P)=(x+y+z)=1.00$ mole, whereas in other cases the reaction mixtures are expressed in terms of molar oxide ratios and may be normalized to 1.00 mole of $P_2O_5$ and/or $Al_2O_3$. This latter form is readily converted to the former form by routine calculations by dividing the total number of moles of "M", aluminum and phosphorous into the moles of each of "M", aluminum and phosphorous. The moles of template and water are similarly normalized by dividing by the total moles of "M", aluminum and phosphorous.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorous, arsenic and antimony, preferably nitrogen or phosphorous and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorous and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine; N-methylethanolamine; N-methylpiperidine; 3-methylpiperidine; n-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2- imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents. The phosphorous source is preferably phosphoric acid, but organic phosphates such as triethyl phosphate may be satisfactory, and so also may crystalline or amorphous aluminophosphates such as the AlPO$_4$ composition of U.S. Pat. No. 4,310,440. Organophosphorous compounds, such as tetrabutylphosphonium bromide, do not apparently serve as reactive sources of phosphorous, but these compounds may function as templating agents. Conventional phosphorous salts such as sodium metaphosphate, may be used, at least in part, as the phosphorous source, but are not preferred.

The aluminum source is preferably either an aluminum alkoxide, such as aluminum isopropoxide, or pseudoboehmite. The crystalline or amorphous aluminophosphates which are a suitable source of phosphorous are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxyates, may be employed including the chlorides, bromides, iodides, nitrates, sulfates, phosphates, acetates, formates, and alkoxides, including ethoxides, propoxides and the like. Specific preferred reagents for introducing various elements "M" are discussed hereinbelow.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, aluminosilicate or molecular sieve compositions, facilitates the crystallization procedure.

After crystallization the ELAPO product may be isolated and advantageously washed with water and dried in air. The as-synthesized ELAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

$$mR:(M_xAl_yP_z)O_2$$

has a value of less than 0.02 other symbols of the formula are as defined hereinabove. In those preparations in which an alkoxide is employed as the source of element "M", aluminum or phosphorous, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized ELAPO material.

Since the present ELAPO compositions are formed from $MO_2^n$, $AlO_2^-$ and $PO_2^+$ tetrahedral oxide units which, respectively, have a net charge of "n", (where "n" may be $-3$, $-2$, $-1$, $0$ or $+1$), the matter of cation exchangeability is considerably more complicated than in the case of zeolitic molecular sieves in which, ideally, there is stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of "M" present in the reaction mixture, or an organic cation derived from the templating agent. Similarly, an $MO_2^n$ tetrahedron, where "n" is negative, can be balanced electrically by association with $PO_2^+$ tetrahedra, a cation of "M" present in the reaction mixture, organic cations derived from the templating agent, a simple cation such as an alkali metal cation, or other divalent or polyvalent metal cation, a proton ($H^+$), or anions of cations introduced from an extraneous source. It has also been postulated that non-adjacent $AlO_2^-$ and $PO_2^+$ tetrahedral pairs can be balanced by $Na^+$ and $OH^-$ respectively (Flanigen and Grose, Molecular Sieve Zeolites-I, ACS, Washington, D.C. (1971).

AsAPO MOLECULAR SIEVES

The AsAPO molecular sieves of U.S. Ser. No. 600,166, filed Apr. 13, 1984, and U.S. Ser. No. 830,889 filed Feb. 19, 1986 have a framework structure of $AsO_2^n$, $AlO_2^-$ and $PO_2^+$ tetrahedral units (where "n" is $-1$ or $+1$) and have an empirical chemical composition on an anhydrous basis expressed by the formula $$mR:(As_xAl_yP_z)O_2$$

wherein "R" represents at least one organic templating agent present in the intracrystalline pore system; "m" represents the molar amount of "R" present per mole of $(As_xAl_yP_z)O_2$ and has a value of zero to about 0.3, but is preferably no greater than 0.15; and "x", "y" and "z" represent the mole fractions of the elements arsenic, aluminum and phosphorous, respectively, present as tetrahedral oxides. The mole fractions "x", "y" and "z" are generally defined as being within the limiting compositional values or points as follows:

|       | Mole Fraction |      |      |
| ----- | ------------- | ---- | ---- |
| Point | x             | y    | z    |
| A     | 0.01          | 0.60 | 0.39 |
| B     | 0.01          | 0.39 | 0.60 |
| C     | 0.39          | 0.01 | 0.60 |
| D     | 0.60          | 0.01 | 0.39 |
| E     | 0.60          | 0.39 | 0.01 |
| F     | 0.39          | 0.60 | 0.01 |

There are two preferred subclasses of the AsAPO molecular sieves, depending upon whether the value of "n" is −1 or +1 (i.e. whether the arsenic is trivalent or pentavalent), it being understood that mixtures of such are permitted in a given AsAPO. When "n" is −1, the preferred values of x, y and z are within the limiting compositional values or points as follows:

|       | Mole Fraction |      |      |
| ----- | ------------- | ---- | ---- |
| Point | x             | y    | z    |
| a     | 0.01          | 0.59 | 0.40 |
| b     | 0.01          | 0.39 | 0.60 |
| c     | 0.39          | 0.01 | 0.60 |
| d     | 0.59          | 0.01 | 0.40 |

When "n" is +1, the preferred values of x, y and z are within the limiting compositional values or points as follows:

|       | Mole Fraction |      |      |
| ----- | ------------- | ---- | ---- |
| Point | x             | y    | z    |
| e     | 0.01          | 0.60 | 0.39 |
| f     | 0.01          | 0.40 | 0.59 |
| g     | 0.59          | 0.40 | 0.01 |
| h     | 0.39          | 0.60 | 0.01 |

In an especially preferred subclass of the AsAPO molecular sieves in which "n" = +1, the values of x, y and z are as follows:

|       | Mole Fraction |      |      |
| ----- | ------------- | ---- | ---- |
| Point | x             | y    | z    |
| i     | 0.03          | 0.52 | 0.45 |
| j     | 0.03          | 0.45 | 0.52 |
| k     | 0.08          | 0.40 | 0.52 |
| l     | 0.33          | 0.40 | 0.27 |
| m     | 0.33          | 0.41 | 0.26 |
| n     | 0.22          | 0.52 | 0.26 |

AsAPO compositions are generally synthesized by hydrothermal crystallization from a reaction mixture containing reactive sources of arsenic, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPO product are obtained, usually a period of from several hours to several weeks. Typical effective times of from 2 hours to about 30 days, generally from about 2 hours to about 20 days, and preferably about 12 hours to about 7 days, have been observed. The product is recovered by any convenient method such as centrifugation or filtration.

In synthesizing the AsAPO compositions, it is preferred to employ a reaction mixture composition expressed in terms of the molar ratios as follows:

$$aR:(As_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "x", "y" and "z" represent the mole fractions of arsenic, aluminum and phosphorous, respectively, and each has a value of at least 0.01.

In one embodiment the reaction mixture is selected such that the mole fractions "x", "y" and "z" are generally defined as being within the limiting compositional values or points as follows:

|       | Mole Fraction |      |      |
| ----- | ------------- | ---- | ---- |
| Point | x             | y    | z    |
| G     | 0.01          | 0.60 | 0.39 |
| H     | 0.01          | 0.39 | 0.60 |
| I     | 0.39          | 0.01 | 0.60 |
| J     | 0.98          | 0.01 | 0.01 |
| K     | 0.39          | 0.60 | 0.01 |

Especially preferred reaction mixtures are those wherein the mole fractions "x", "y" and "z" are within the limiting compositional values or points as follows:

|       | Mole Fraction |      |      |
| ----- | ------------- | ---- | ---- |
| Point | x             | y    | z    |
| a     | 0.20          | 0.55 | 0.25 |
| b     | 0.20          | 0.50 | 0.30 |
| c     | 0.30          | 0.40 | 0.30 |
| d     | 0.40          | 0.40 | 0.20 |
| e     | 0.40          | 0.50 | 0.10 |
| f     | 0.35          | 0.55 | 0.10 |

In the foregoing expression of the reaction composition, the reactants are normalized with respect to the total of "x", "y" and "z" such that $(x+y+z) = 1.00$ mole. Molecular sieve containing arsenic, aluminum and phosphorous as framework tetrahedral oxide units are prepared as follows:

Preparative Reagents

AsAPO compositions may be prepared by using numerous reagents. Reagents which may be employed to prepare AsAPOs include:
(a) aluminum isopropoxide;
(b) pseudoboehmite or other aluminum oxide;
(c) $H_3PO_4$: 85 weight percent aqueous phosphoric acid;
(d) $As_2O_5$, arsenic (V) oxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_3H_7)$;

(j) MQuin: Methyl Quinuclidine hydroxide, ($C_7H_{13}NCH_3OH$);
(k) C-hex: cyclohexylamine;
(l) TMAOH: tetramethylammonium hydroxide
(m) TPAOH: tetrapropylammonium hydroxide; and
(n) DEEA: 2-diethylaminoethanol.

Preparative Procedures

AsAPOs may be prepared by forming a starting reaction mixture by dissolving the arsenic (V) oxide and the $H_3PO_4$ in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BAPO MOLECULAR SIEVES

The BAPO molecular sieves of U.S. Ser. No. 599,812, filed Apr. 13, 1984, U.S. Ser. No. 804,248, filed Dec. 4, 1985, and U.S. Ser. No. 029,540, filed Mar. 24, 1987, have a framework structure of $BO_2^-$, $AlO_2^-$ and $PO_2^+$ tetrahedral units and have an empirical chemical composition on an anhydrous basis expressed by the formula:

$$mR:(B_xAl_yP_z)O_2$$

wherein "R" represents at leas one organic templating agent present in the intracrystalline pore system; "m" represents the molar amount of "R" present per mole of $(B_xAl_yP_z)O_2$ and has a value of zero to about 0.3, "x", "y" and "z" represent the mole fractions of the elements boron, aluminum and phosphorus, respectively, present as tetrahedral oxides. The more fractions "x", "y" and "z" are generally defined as being within the limiting compositional values or points as follows:

| Point | Mole Fraction | | |
|-------|------|------|------|
|       | x    | y    | z    |
| A     | 0.01 | 0.60 | 0.39 |
| B     | 0.01 | 0.39 | 0.60 |
| C     | 0.39 | 0.01 | 0.60 |
| D     | 0.60 | 0.01 | 0.39 |
| E     | 0.60 | 0.39 | 0.01 |
| F     | 0.39 | 0.60 | 0.01 |

In a preferred subclass of the BAPO molecular sieves the values of x, y, and z are within the limiting compositional values or points as follows:

| Point | Mole Fraction | | |
|-------|------|------|------|
|       | x    | y    | z    |
| a     | 0.01 | 0.59 | 0.40 |
| b     | 0.01 | 0.39 | 0.60 |
| c     | 0.39 | 0.01 | 0.60 |
| d     | 0.59 | 0.01 | 0.40 |

An especially preferred subclass of the BAPO molecular sieves are those in which the mole fraction, "x", of boron is not greater than about 0.3.

BAPO compositions are generally synthesized by hydrothermal crystallization from a reaction mixture containing reactive sources of boron, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BAPO product are obtained, usually a period of from several hours to several weeks. Typical effective times of from 2 hours to about 30 days, generally from about 4 hours to about 14 days, and preferably about 1 to about 7 days, have been observed. The product is recovered by any convenient method such as centrifugation or filtration.

In synthesizing the BAPO compositions, it is preferred to employ a reaction mixture composition expressed in terms of the molar ratios as follows:

$$aR:(B_xAl_yP_z)O_2:bH_2O$$

where "R" is an organic templating agent; "a" is the amount of organic templating agent "R" and is an effective amount preferably within the range of greater than zero (0) to about 6, and most preferably not more than about 1.0; "b" has a value of from zero (0) to about 500, preferably between about 2 and about 300, desirably not greater than about 20, and most desirably not greater than about 10; and "x", "y" and "z" represent the mole fractions of boron, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|-------|------|------|------|
|       | x    | y    | z    |
| G     | 0.01 | 0.60 | 0.39 |
| H     | 0.01 | 0.39 | 0.60 |
| I     | 0.39 | 0.01 | 0.60 |
| J     | 0.98 | 0.01 | 0.01 |
| K     | 0.39 | 0.60 | 0.01 |

Especially preferred reaction mixtures are those containing from 0.5 to 2.0 moles of $B_2O_3$ and from 0.75 to 1.25 moles of $Al_2O_3$ for each mole of $P_2O_5$.

In the foregoing expression of the reaction composition, the reactants are normalized with respect to the total of "x", "y" and "z" such that (x+y+z)=1.00 mole.

The exact nature of the BAPO molecular sieves is not entirely understood at present, although all are believed to contain $BO_2$, $AlO_2$ and $PO_2$ tetrahedra in the three-dimensional microporous framework structure. The low level of boron present in some of the instant molecular sieves makes it difficult to ascertain the exact nature of the interactions among boron, aluminum and phosphorus. As a result, although it is believed that $BO_2$ tetrahedra are present in the three-dimensional microporous framework structure, it is appropriate to characterize certain BAPO compositions in terms of the molar ratios of oxides.

Molecular sieves containing boron, aluminum and phosphorus as framework tetrahedral oxide units are prepared as follows:

Preparative Reagents

BAPO compositions may be prepared by using numerous reagents. Reagents which may be employed to prepare BAPOs include:
(a) aluminum isopropoxide;
(b) pseudoboehmite or other aluminum oxide;
(c) $H_3PO_4$: 85 wieght percent aqueous phosphoric acid;
(d) boric acid or trimethylborate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinulidine, $(C_7H_{13}N)$,
(j) MQuin: Methyl Quinuclide hydroxide, $(C_7H_{13}NCH_3OH)$;
(k) c-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

In the preferred method of synthesizing the BAPO compositions, one first combines sources of boron, aluminum and phosphorus to form an amorphous material containing all three elements, and thereafter heats the amorphous material to produce a crystalline BAPO molecular sieve. It is not necessary that the total quantities of the reactive sources of boron, aluminum and phosphorus to be used in the final reaction mixture be present in the amorphous material, since additional quantities of the elements can be added during the later heat treatment; in particular, it has been found convenient to add additional quantities of phosphorus to the amorphous material before the heat treatment. The preliminary formation of the amorphous material assists in the incorporation of the boron into the final molecular sieve.

For example, BAPOs may be prepared by forming a solution of boric acid in a methanolic solution of the templating agent, then adding a hydrated aluminosphosphate and water and stirring to form a homogeneous reaction slurry. This slurry is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPO MOLECULAR SIEVES

The BeAPO molecular sieves of U.S. Ser. No. 599,776, filed Apr. 13, 1984, and U.S. Ser. No. 835,293 filed Mar. 3, 1986 have a framework structure of $BeO_2^{-2}$, $AlO_2^-$ and $PO_2^+$ tetrahedral units and have an empirical chemical composition on an anhydrous basis expressed by the formula:

wherein "R" represents at least one organic templating agent present in the intracrystalline pore system; "m" represents the molar amount of "R" present per mole of $(Be_xAl_yP_z)O_2$ and has a value of zero to about 0.3, but is preferably not greater than 0.15; and "x", "y" and "z" represent the mole fractions of the elements beryllium, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the BeAPO molecular sieves the values of x, y and z are within the limiting compositional values or points as follows:

| Point | Mole Fraction | | |
|---|---|---|---|
| | x | y | z |
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In an especially preferred subclass of molecular sieves the values of x, y and z are as follows:

| Point | Mole Fraction | | |
|---|---|---|---|
| | x | y | z |
| e | 0.02 | 0.46 | 0.52 |
| f | 0.10 | 0.38 | 0.52 |
| g | 0.10 | 0.46 | 0.44 |

BeAPO compositions are generally synthesized by hydrothermal crystallization from a reaction mixture containing reactive sources of beryllium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BeAPO product are obtained, usually a period of from several hours to several weeks. Typical effective times of from 2 hours to about 30 days, generally from about 4 hours to about 14 days, and preferably about 1 to about 7 days, have been observed. The product is recovered by any convenient method such as centrifugation or filtration.

In synthesizing the BeAPO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6, and most preferably not more than about 1.5;

"b" has a value of from zero (0) to about 500, preferably between about 2 and about 300, most preferably not greater than about 50; and "x", "y" and "z" represent the mole fractions of beryllium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those wherein the mole fractions "x", "y" and "z" are within the limiting compositional values or points as follows:

| Point | Mole Fraction | | |
|---|---|---|---|
| | x | y | z |
| g | 0.04 | 0.46 | 0.50 |
| h | 0.16 | 0.34 | 0.50 |
| i | 0.17 | 0.34 | 0.49 |
| j | 0.17 | 0.43 | 0.40 |
| k | 0.14 | 0.46 | 0.40 |

In the foregoing expression of the reaction composition, the reactants are normalized with respect to the total of "x", "y" and "z" such that $(x+y+z)=1.00$ mole. Molecular sieves containing beryllium, aluminum and phosphorus as framework tetrahedral oxide units are prepared as follows:

Preparative Reagents

BeAPO compositions may be prepared by using numerous reagents. Reagents which may be employed to prepare BeAPOs include:
(a) aluminum isopropoxide;
(b) pseudoboehmite or other aluminum oxide;
(c) $H_3PO_4$:85 weight percent aqueous phosphoric acid;
(d) beryllium sulfate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclide hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

BeAPOs may be prepared by forming a starting reaction mixture by dissolving the beryllium sulfate and the $H_3PO_4$ in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C. for a time or placed in lined screw top bottles for digestion at 100° C. Digestions are typically carried out under autogenous pressure.

CAPO MOLECULAR SIEVES

The CAPO molecular sieves of U.S. Ser. No. 599,813, filed Apr. 13, 1984, and U.S. Ser. No. 830,756 filed Feb. 19, 1986 have a framework structure of $CrO_2{}^n$, $AlO_2{}^-$ and $PO_2{}^+$ tetrahedral units (where "n" is $-1$, 0 or $+1$) and have an empirical chemical composition on an anhydrous basis expressed by the formula $$mR:(Cr_xAl_yP_z)O_2$$

wherein "R" represents at least one organic templating agent present in the intracrystalline pore system; "m" represents the molar amount of "R" present per mole of $(Cr_xAl_yP_z)O_2$ and has a value of zero to about 0.3, but is preferably not greater than 0.15; and "x", "y" and "z" represent the mole fractions of the elements chromium, aluminum and phosphorus, respectively, present as tetrahedral oxides. When "n" is $-1$ or $+1$, the mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

When "n" is 0, the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.47 | 0.52 |
| I | 0.94 | 0.01 | 0.05 |
| J | 0.98 | 0.01 | 0.01 |
| K | 0.39 | 0.60 | 0.01 |

There are three preferred subclasses of the CAPO molecular sieves, depending upon whether the value of "n" is $-1$, 0 or $+1$ (i.e. whether the chromium has an oxidation number of 3, 4, or 5), it being understood that mixtures of such are permitted in a given CAPO. When "n" is $-1$, the preferred values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

In an especially preferred subclass of these CAPO molecular sieves in which "n" = −1, the values of x, y and z are as follows:

| Point | Mole Fraction | | |
|---|---|---|---|
| | x | y | z |
| n | 0.01 | 0.52 | 0.47 |
| o | 0.01 | 0.42 | 0.57 |
| p | 0.03 | 0.40 | 0.57 |
| q | 0.07 | 0.40 | 0.53 |
| r | 0.07 | 0.47 | 0.46 |
| s | 0.02 | 0.52 | 0.46 |

When "n" is 0, the preferred values of x, y and z are within the limiting compositional values or points as follows:

| Point | Mole Fraction | | |
|---|---|---|---|
| | x | y | z |
| e | 0.01 | 0.60 | 0.39 |
| f | 0.01 | 0.47 | 0.52 |
| g | 0.50 | 0.225 | 0.275 |
| h | 0.50 | 0.40 | 0.10 |
| i | 0.30 | 0.60 | 0.10 |

When "n" is +1, the preferred values of x, y and z are within the limiting compositional values or points as follows:

| Point | Mole Fraction | | |
|---|---|---|---|
| | x | y | z |
| j | 0.01 | 0.60 | 0.39 |
| k | 0.01 | 0.40 | 0.59 |
| l | 0.59 | 0.40 | 0.01 |
| m | 0.39 | 0.60 | 0.10 |

Since the exact nature of the CAPO molecular sieves is not clearly understood at present, although all are believed to contain $CrO_2$ tetrahedra in the three-dimensional microporous crystal framework structure, it is advantageous to characterize the CAPO molecular sieves by means of their chemical composition. This is due to the low level of chromium present in certain of the CAPO molecular sieves prepared to date which makes it difficult to ascertain the exact nature of the interaction between chromium, aluminum and phosphorous. As a result, although it is believed that $CrO_2$ tetrahedra are substituted isomorphously for $AlO_2$ or $PO_2$ tetrahedra, it is appropriate to characterize certain CAPO compositions by reference to their chemical composition in terms of the mole ratios of oxides.

CAPO compositions are generally synthesized by hydrothermal crystallization from a reaction mixture containing reactive sources of chromium, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the CAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the CAPO compositions, it is preferred to employ a reaction mixture composition expressed in terms of the molar ratios as follows:

$$aR:(Cr_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably not greater than about 20; and "x", "y" and "z" represent the mole fractions of chromium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| L | 0.01 | 0.60 | 0.39 |
| M | 0.01 | 0.39 | 0.60 |
| N | 0.39 | 0.01 | 0.60 |
| O | 0.98 | 0.01 | 0.01 |
| P | 0.39 | 0.60 | 0.01 |

Especially preferred reaction mixtures are those containing from about 0.1 to about 0.4 moles of chromium, and from about 0.75 to about 1.25 moles of aluminum, per mole of phosphorous.

In the foregoing expression of the reaction composition, the reactants are normalized with respect to the total of "x", "y" and "z" such that (x+y+z)=1.00 mole. Molecular sieves containing chromium, aluminum and phosphorous as framework tetrahedral oxide units are prepared as follows:

Preparative Reagents

CAPO compositions may be prepared by using numerous reagents. Reagents which may be employed to prepare CAPOs include:

(a) aluminum isopropoxide, or aluminum chlorhydrol;
(b) pseudoboehmite or other aluminum oxide;
(c) $H_3PO_4$: 85 weight percent aqueous phosphoric acid;
(d) chromium (III) orthophosphate, chromium (III) acetate and chromium acetate hydroxide, $(Cr_3(OH)_2(CH_3COO)_7)$;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide:
(m) TPAOH: tetrapropylammonium hydroxide; and
(n) DEEA: 2-diethylaminoethanol.

Preparative Procedures

CAPOs may be prepared by forming a starting reaction mixture by adding aluminum chlorhydrol or aluminum oxide to a solution of chromium acetate hydroxide in water, then adding successively phosphoric acid and the templating agent. Between each addition, and after formation of the final mixture, the mixture is blended until a homogeneous mixture is observed.

Alternatively, the phosphoric acid may be mixed with at least part of the water, and aluminum oxide or isopropoxide mixed in. A solution of chromium acetate hydroxide is then added, followed by the templating agent, and the resultant mixture mixed until homogeneous.

In a third procedure, amorphous chromium phosphate is ground dry with aluminum oxide and the resultant dry mixture added to an aqueous solution of phosphoric acid in an ice bath. The templating agent is then added, and the final mixture mixed until homogenous.

Whichever technique is employed to produce the reaction mixture, this mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPO MOLECULAR SIEVES

The GaAPO molecular sieves of U.S. Ser. No. 599,771, filed Apr. 13, 1984, and U.S. Ser. No. 830,890 filed Feb. 19, 1986 have a framework structure of $GaO_2^-$, $AlO_2^-$ and $PO_2^+$ tetrahedral units and have an empirical chemical composition on an anhydrous basis expressed by the formula:

$$mR:(Ga_xAl_yP_z)O_2$$

wherein "R" represents at least one organic templating agent present in the intracrystalline pore system; "m" represents the molar amount of "R" present per mole of $(G_xAl_yP_z)O_2$ and has a value of zero to about 0.3, but is preferably not greater than 0.15; and "x", "y" and "z" represent the mole fractions of the elements gallium, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.34 | 0.65 |
| C | 0.34 | 0.01 | 0.65 |
| D | 0.60 | 0.01 | 0.39 |
| E | 0.60 | 0.39 | 0.01 |
| F | 0.39 | 0.60 | 0.01 |

In general, the value of "z" in the GaAPO molecular sieves is not greater than about 0.60.

In a preferred subclass of the GaAPO molecular sieves the values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.34 | 0.65 |
| c | 0.34 | 0.01 | 0.65 |
| d | 0.59 | 0.01 | 0.40 |

In an especially preferred subclass of the GaAPO molecular sieves the values of x, y and z are as follows:

| Point | Mole Fraction | | |
|---|---|---|---|
| | x | y | z |
| e | 0.03 | 0.52 | 0.45 |
| f | 0.03 | 0.33 | 0.64 |
| g | 0.16 | 0.20 | 0.64 |
| h | 0.25 | 0.20 | 0.55 |
| i | 0.25 | 0.33 | 0.42 |
| j | 0.06 | 0.52 | 0.42 |

GaAPO compositions are generally synthesized by hydrothermal crystallization from a reaction mixture containing reactive sources of gallium, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPO product are obtained, usually a period of from several hours to several weeks. Typical effective times of from 2 hours to about 30 days, generally from about 4 hours to about 20 days, and preferably about 1 to about 7 days, have been observed. The product is recovered by any convenient method such as centrifugation or filtration.

In synthesizing the GaAPO compositions, it is preferred to employ a reaction mixture composition expressed in terms of the molar ratios as follows:

$$aR:(Ga_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably between about 2 and 20; and "x", "y" and "z" represent the mole fractions of gallium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |

| Point | Mole Fraction | | |
|---|---|---|---|
| | x | y | z |
| K | 0.39 | 0.60 | 0.01 |

Especially preferred reaction mixtures are those containing from 0.2 to 0.5 mole of $Ga_2O_3$ and from 0.3 to 1 mole of $Al_2O_3$ for each mole of $P_2O_5$.

In the foregoing expression of the reaction composition, the reactants are normalized with respect to the total of "x", "y" and "z" such that $(x+y+z)=1.00$ mole. Molecular sieves containing gallium, aluminum and phosphorous as framework tetrahedral oxide units are prepared as follows:

Preparative Reagents

GaAPO compositions may be prepared by using numerous reagents. Reagents which may be employed to prepare GaAPOs include:
(a) aluminum isopropoxide;
(b) pseudoboehmite or other aluminum oxide;
(c) $H_3PO_4$: 85 weight percent aqueous phosphoric acid;
(d) gallium sulfate or gallium (III) hydroxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

GaAPOs may be prepared by forming a starting reaction mixture by mixing the phosphoric acid with at least part of the water. To this solution the aluminum oxide or isopropoxide is added. This mixture is then blended until a homogenous mixture is observed. To this mixture the gallium sulfate or gallium hydroxide and the templating agent are successively added and the resulting mixture blended until a homogeneous mixture is observed.

Alternatively, the aluminum oxide may be mixed with a solution of the gallium sulfate or hydroxide, and then the phosphoric acid and the templating agent successively added. The resulting mixture is then blended until a homogeneous mixture is observed.

In a third process, the templating agent may be dissolved in water, the gallium hydroxide or sulfate added with stirring, a solution of the phosphoric acid added, and finally the aluminum oxide mixed in. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressures.

GeAPO MOLECULAR SIEVES

The GeAPO molecular sieves of U.S. Ser. No. 599,807, filed Apr. 13, 1984, and U.S. Ser. No. 841,753 filed Mar. 20, 1986 have a framework structure of $GeO_2$, $AlO_2^-$ and $PO_2^+$ tetrahedral units and have an empirical chemical composition on an anhydrous basis expressed by the formula:

$$mR:(Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3, but is preferably no greater than 0.2; and "x", "y" and "z" represent the mole fractions of the elements germanium, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01 |

In a preferred subclass of the GeAPO molecular sieves the values of x, y and z are within the limiting compositional values or points as follows:

| Point | Mole Fraction | | |
|---|---|---|---|
| | x | y | z |
| a | 0.01 | 0.60 | 0.39 |
| b | 0.01 | 0.47 | 0.52 |
| c | 0.50 | 0.225 | 0.275 |
| d | 0.50 | 0.40 | 0.10 |
| e | 0.30 | 0.60 | 0.10 |

An especially preferred subclass of the GeAPO molecular sieves are those in which the value of "x" is not greater than about 0.13.

GeAPO compositions are generally synthesized by hydrothermal crystallization from a reaction mixture containing reactive sources of germanium, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GeAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the GeAPO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably between about 10 and about 60; and "x", "y" and "z" represent the mole fractions of germanium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Especially preferred reaction mixtures are those containing from 0.2 to 0.4 mole of GeO$_2$ and from 0.75 to 1.25 mole of Al$_2$O$_3$ for each mole of P$_2$O$_5$.

In the foregoing expression of the reaction composition, the reactants are normalized with respect to the total of "x", "y" and "z" such that (x+y+z)=1.00 mole. Molecular sieves containing germanium, aluminum and phosphorous as framework tetrahedral oxide units are prepared as follows:

Preparative Reagents

GeAPO compositions may be prepared by using numerous reagents. Reagents which may be employed to prepare GeAPOs include:
(a) aluminum isopropoxide;
(b) pseudoboehmite or other aluminum oxide;
(c) H$_3$PO$_4$: 85 weight percent aqueous phosphoric acid;
(d) germanium tetrachloride, germanium ethoxide and germanium dioxide;
(e) TEAOH: 40 weight percent aqueous solution of tetraethylammonium hydroxide;
(f) TBAOH: 40 weight percent aqueous solution of tetrabutylammonium hydroxide;
(g) Pr$_2$NH: di-n-propylamine, (C$_3$H$_7$)$_2$NH;
(h) Pr$_3$N: tri-n-propylamine, (C$_3$H$_7$)$_3$N;
(i) Quin: Quinuclidine, (C$_7$H$_{13}$N);
(j) MQuin: Methyl Quinuclidine hydroxide, (C$_7$H$_{13}$NCH$_3$OH);
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

In some cases, it may be advantageous, when synthesizing the GeAPO compositions, to first combine sources of germanium and aluminum, to form a mixed germanium/aluminum compound (this compound being typically a mixed oxide) and thereafter to combine this mixed compound with a source of phosphorous to form the final GeAPO composition. Such mixed oxides may be prepared for example by hydrolyzing aqueous solutions containing germanium tetrachloride and aluminum chlorhydrol, or aluminum tri-sec-butoxide.

GeAPOs may be prepared by forming a starting reaction mixture by mixing the phosphoric acid with at least part of the water. To this solution is added the mixed germanium/aluminum oxide prepared as described above. This mixture is then blended until a homogeneous mixture is observed. To this mixture the templating agent is added and the resulting mixture blended until a homogeneous mixture is observed.

Alternatively, to a solution of aluminum isopropoxide may be added germanium ethoxide. The resultant solution may optionally be dried to produce a mixed oxide. To the mixed solution or dried oxide are added successively the phosphoric acid and the templating agent. The resulting mixture is then blended until a homogeneous mixture is observed.

In a third process, a solution is formed by dissolving the phosphoric acid in water, adding aluminum oxide or isopropoxide and mixing thoroughly. To the resultant mixture is added a solution containing the templating agent and germanium dioxide. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

LiAPO MOLECULAR SIEVES

The LiAPO molecular sieves of U.S. Ser. No. 599,811, filed Apr. 13, 1984, and U.S. Ser. No. 834,921 filed Feb. 28, 1986 have a framework structure of LiO$_2^{-3}$, AlO$_2^-$ and PO$_2^+$ tetrahedral units and have an empirical chemical composition on an anhydrous basis expressed by the formula:

wherein "R" represents at least one organic templating agent present in the intracrystalline pore system; "m" represents the molar amount of "R" present per mole of (Li$_x$Al$_y$P$_z$)O$_2$ and has a value of zero to about 0.3, but is preferably not greater than 0.15; and "x", "y" and "z" represent the mole fractions of the elements lithium, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the LiAPO molecular sieves the values of x, y and z are within the limiting compositional values or points as follows:

| Point | Mole Fraction x | y | z |
|---|---|---|---|
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In an especially preferred subclass of the LiAPO molecular sieves the values of x, y and z are within the following limits:

| Point | Mole Fraction x | y | z |
|---|---|---|---|
| e | 0.01 | 0.52 | 0.47 |
| f | 0.01 | 0.47 | 0.52 |
| g | 0.03 | 0.45 | 0.52 |
| h | 0.10 | 0.45 | 0.45 |
| i | 0.10 | 0.49 | 0.41 |
| j | 0.07 | 0.52 | 0.41 |

LiAPO compositions are generally synthesized by hydrothermal crystallization from a reaction mixture containing reactive sources of lithium, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the LiAPO product are obtained, usually a period of from several hours to several weeks. Typical effective times of from 2 hours to about 30 days, generally from about 12 hours to about 5 days, have been observed. The product is recovered by any convenient method such as centrifugation or filtration.

In synthesizing the LiAPO compositions, it is preferred to employ a reaction mixture composition expressed in terms of the molar ratios as follows:

$$aR:(Li_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 2; "b" has a value of from zero (0) to about 500, preferably between 2 and 300, most preferably not greater than about 40; and "x", "y" and "z" represent the mole fractions of lithium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction x | y | z |
|---|---|---|---|
| G | 0.01 | 0.60 | 0.39 |
| H | 0.01 | 0.39 | 0.60 |
| I | 0.39 | 0.01 | 0.60 |
| J | 0.98 | 0.01 | 0.01 |

| Point | Mole Fraction x | y | z |
|---|---|---|---|
| K | 0.39 | 0.60 | 0.01 |

In an especially preferred subclass of the reaction mixtures, the values of "x", "y" and "z" are within the limiting compositional values or points as follows:

| Point | Mole Fraction x | y | z |
|---|---|---|---|
| l | 0.03 | 0.50 | 0.47 |
| m | 0.03 | 0.45 | 0.52 |
| n | 0.08 | 0.40 | 0.52 |
| o | 0.10 | 0.40 | 0.50 |
| q | 0.04 | 0.50 | 0.46 |

In the foregoing expression of the reaction composition, the reactants are normalized with respect to the total of "x", "y" and "z" such that $(x+y+z)=1.00$ mole.

Since the exact nature of the LiAPO molecular sieves is not clearly understood at present, although all are believed to contain $LiO_2$ tetrahedra in the three-dimensional microporous crystal framework structure, it is advantageous to characterize the LiAPO molecular sieves by means of their chemical composition. This is due to the low level of lithium present in certain of the LiAPO molecular sieves prepared to date which makes it difficult to ascertain the exact nature of the interaction between lithium, aluminum and phosphorous. As a result, although it is believed that $LiO_2$ tetrahedra are substituted isomorphously for $AlO_2$ or $PO_2$ tetrahedra, it is appropriate to characterize certain LiAPO compositions by reference to their chemical composition in terms of the mole ratios of oxides.

Molecular sieves containing lithium, aluminum and phosphorous as framework tetrahedral oxide units are prepared as followed:

Preparative Reagents

LiAPO compositions may be prepared by using numerous reagents. Reagents which may be employed to prepare LiAPOs include:
(a) aluminum isopropoxide;
(b) pseudoboehmite or other aluminum oxide;
(c) $H_3PO_4$:85 weight percent aqueous phosphoric acid;
(d) lithium sulfate or lithium orthophosphate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

LiAPOs may be prepared by forming a starting reaction mixture by suspending aluminum oxide in at least part of the water. To this mixture the templating agent is added. The resultant mixture is then blended until a homogeneous mixture is observed. To this mixture the lithium phosphate or sulfate is added and the resulting mixture blended until a homogeneous mixture is observed. Alternatively, an initial mixture may be formed by mixing aluminum oxide and lithium phosphate or sulfate. To the resultant mixture are added successively phosphoric acid and an aqueous solution of the templating agent, and the resulting mixture blended until a homogeneous mixture is observed.

In a third procedure, the phosphoric acid is mixed with at least part of the water, and the aluminum oxide is mixed in. To the resultant mixture are added lithium sulfate and the templating agent, and the resulting mixture blended until a homogeneous mixture is observed.

Whichever procedure is adopted to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

FeTiAPO MOLECULAR SIEVES

The FeTiAPO molecular sieves of U.S. Ser. No. 599,824, filed Apr. 13, 1984, and U.S. Ser. No. 902,129 filed Sept. 2, 1986 have three-dimensional microporous framework structures of $FeO_2^n$, $TiO_2$, $AlO_2^-$ and $PO_2^+$ tetrahedral oxide units, where "n" is $-2$ or $-1$, and have an empirical chemical composition on an anhydrous basis expressed by the formula:

$$mR: (M_xAl_yP_z)O_2$$

wherein "R" represents at least one organic templating agent present in the intracrystalline pore system; "M" represents iron and titanium: "m" represents the molar amount of "R" present per mole of $(M_xAl_yP_z)O_2$ and has a value of zero (0) to about 0.3: and "x", "y" an "z" represent the mole fractions of "M", aluminum and phosphorus, respectively present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the FeTiAPO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

FeTiAPO compositions are generally synthesized by hydrothermal crystallization from a reaction mixture containing reactive sources of iron, titanium, aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the FeTiAPO product are obtained, usually a period of from several hours to several weeks. Typical effective times of from 2 hours to about 30 days, generally from about 12 hours to about 5 days, have been observed. The product is recovered by any convenient method such as centrifugation or filtration.

In synthesizing the FeTiAPO compositions, it is preferred to employ a reaction mixture composition expressed in terms of the molar ratios as follows:

$$aR: (M_xAl_yP_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "x", "y" and "z" represent the mole fractions of "M" (iron and titanium), aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to the total of "x", "y" and "z" such that $(x+y+z)=1.00$ mole.

Molecular sieves containing iron, titanium, aluminum and phosphorous as framework tetrahedral oxide units are prepared as follows:

Preparative Reagents

FeTiAPO compositions may be prepared by using numerous reagents. The preferred sources of iron and titanium for preparing FeTiAPOs are the same as those for preparing the FeAPOs and TiAPOs already described above. Other reagents which may be employed to prepare FeTiAPOs include:

(a) aluminum isopropoxide;
(b) pseudoboehmite or other aluminum oxide;
(c) $H_3PO_4$: 85 weight percent aqueous phosphoric acid;
(d) TEAOH: 40 weight percent aqueous solution of tetraethylammonium hydroxide;
(e) TBAOH: 40 weight percent aqueous solution of tetrabutylammonium hydroxide;

(f) Pr₂NH: di-n-propylamine, (C₃H₇)₂NH;
(g) Pr₃N: tri-n-propylamine, (C₃H₇)₃N;
(h) Quin: Quinuclidine, (C₇H₁₃N);
(i) MQuin: Methyl Quinuclidine hydroxide, (C₇H₁₃NCH₃OH);
(j) C-hex: cyclohexylamine;
(k) TMAOH: tetramethylammonium hydroxide;
(l) TPAOH: tetrapropylammonium hydroxide; and
(m) DEEA: 2-diethylaminoethanol.

Preparative Procedures

FeTiAPOs may be prepared by forming a homogeneous reaction mixture containing reactive sources of iron, titanium, aluminum and phosphorous. The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

XAPO MOLECULAR SIEVES

The XAPO molecular sieves of U.S. Ser. No. 599,810, filed Apr. 13, 1984, and U.S. Ser. No. 902,020 filed Sept. 2, 1986 have a three-dimensional microporous framework structure of $MO_2^n$, $AlO_2$ and $PO_2^{30}$ tetrahedral oxide units, where "n" is 0, −1 or −2, and have an empirical chemical composition on an anhydrous basis expressed by the formula:

mR: $(M_xAl_yP_z)O_2$ wherein "R" represents at least one organic templating agent present in the intracrystalline pore system; "M" represents at least one element from each of the classes of: 1) iron and titanium; and 2) cobalt, magnesium, manganese and zinc; "n" is 0, −1 or −2; "m" represents a molar amount of "R" present per mole of $(M_xAl_yP_z)O_2$ and has a value of zero (0) to about 0.3; and "x", "y" and "z" represent the mole fractions of "M", aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the XAPO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

XAPO compositions are generally synthesized by hydrothermal crystallization from a reaction mixture containing reactive sources of "M", aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the XAPO product are obtained, usually a period of from several hours to several weeks. Typical effective times of from 2 hours to about 30 days, generally from about 2 hours to about 20 days, have been observed. The product is recovered by any convenient method such as centrifugation or filtration.

In synthesizing the XAPO compositions, it is preferred to employ a reaction mixture composition expressed in terms of the molar ratios as follows:

aR: $(M_xAl_yP_z)O_2$: bH₂O wherein "R" is an organic templating agent; "a" is the amount of organic templating agent "R" and has a value of from zero to about 6 and is preferably an effective amount within the range of greater than zero (0) to about 6; "M" represents at least one element from each of the classes of: 1) iron and titanium; and 2) cobalt, magnesium, manganese and zinc; "b" has a value of from zero (0) to about 500, preferably between about 2 and about 300; and "x", "y" and "z" represent the mole fractions of "M" (iron and/or titanium, and at least one of cobalt, magnesium, manganese and zinc), aluminum and phosphorous, respectively, and each has a value of at least 0.01, with the proviso that "x" has a value of at least 0.02.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to the total of "x", "y" and "z" such that (x+y+z)=1.00 mole.

XAPO molecular sieves are prepared as follows:

Preparative Reagents

XAPO compositions may be prepared by using numerous reagents. The preferred sources of elements "M" for preparing XAPOs are the same as those for preparing other APOs containing the same elements, as described above and below. Other reagents which may be employed to prepare XAPOs include:
(a) aluminum isopropoxide;
(b) pseudoboehmite or other aluminum oxide;
(c) H₃PO₄: 85 weight percent aqueous phosphoric acid;

(d) TEAOH: 40 weight percent aqueous solution of tetraethylammonium hydroxide;
(e) TBAOH: 40 weight percent aqueous solution of tetrabutylammonium hydroxide;
(f) Pr₂NH: di-n-propylamine, $(C_3H_7)_2NH$;
(g) Pr₃N: tri-n-propylamine, $(C_3H_7)_3N$
(h) Quin: Quinuclidine, $(C_7H_{13}N)$;
(i) MQuin: Methyl Quinuclidine hydroxide, $(C_7H_{13}NCH_3OH)$;
(j) C-hex: cyclohexylamine;
(k) TMAOH: tetramethylammonium hydroxide
(l) TPAOH: tetrapropylammonium hydroxide; and
(m) DEEA: 2-diethylaminoethanol.

Preparative Procedures

XAPOs may be prepared by forming a homogenous reaction mixture containing reactive sources of element "M", aluminum and phosphorous. The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

MIXED-ELEMENT APO MOLECULAR SIEVES

The mixed element APO molecular sieves of U.S. Ser. No. 599,978, filed Apr.13, 1984, and U.S. Ser. No. 846,088 filed Mar. 31, 1986 have a framework structure of $MO_2^n$, $AlO_2^-$ and $PO_2^{30}$ tetrahedral units, wherein $MO_2^n$ represents at least two different elements present as tetrahedral units "$MO_2^n$" with charge "n", where "n" may be −3, −2, −1, or 0 or +1. One of the elements "M" is selected from the group consisting of arsenic, beryllium, boron, chromium, gallium, germanium, lithium and vanadium, while a second one of the elements "M" is selected from the group consisting of cobalt, iron, magnesium, manganese, titanium and zinc. Preferably, "M" is a mixture of lithium and magnesium. The mixed-element molecular sieves have an empirical chemical composition on an anhydrous basis expressed by the formula:

mR: $(M_xAl_yP_z)O_2$ wherein "R" represents at least one organic templating agent present in the intracrystalline pore system; "m" represents the molar amount of "R" present per mole of

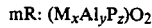aR: $(M_xAl_yP_z)O_2$ and has a value of zero to about 0.3, but is preferably not greater than 0.15; and "x", "y" and "z" represent the mole fractions of the elements "M" (i.e. "x" is the total of the mole fractions of the two or more elements "M"), aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the mixed-element APO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

An especially preferred subclass of the mixed-element APO molecular sieves are those in which the value of x is not greater than about 0.10.

A second group (FCAPO's) of mixed element APO molecular sieves are described in U.S. Pat. No. 4,686,093 issued Aug. 11, 1987 (incorporated herein by reference). The mixed-element APO compositions are generally synthesized by hydrothermal crystallization from a reaction mixture containing reactive sources of the elements "M", aluminum and phosphorous, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the APO product are obtained, usually a period of from several hours to several weeks. Typical effective times of from 2 hours to about 30 days, generally from about 2 hours to about 20 days, and preferably about 12 hours to about 5 days, have been observed. The product is recovered by any convenient method such as centrifugation or filtration.

In synthesizing the mixed-element APO compositions, it is preferred to employ a reaction mixture composition expressed in terms of the molar ratios as follows:

aR: $(M_xAl_yP_z)O_2$: $bH_2O$ wherein "R" is an organic templating agent; "a" is the amount of organic templating agent "R" and has a value of from zero to about 6 and is preferably an effective amount within the range of greater than zero (0) to about 6, and most preferably not more than 0.5; "b" has a value of from zero (0) to about 500, preferably between about 2 and about 300, most preferably not greater than about 20, and most desirably not more than about 10; and "x", "y" and "z" represent the mole fractions of "M", aluminum and phosphorous, respectively, "y" and "z" each having a value of at least 0.01 and "x" having a value of at least 0.02, with each element "M" having a mole fraction of at least 0.01.

In one embodiment the reaction mixture is selected such that the mole fractions "x", "y" and "z" are generally defined as being within the limiting compositional values or points as follows:

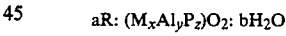

| Point | Mole Fraction | | |
|---|---|---|---|
| | x | y | z |
| F | 0.02 | 0.60 | 0.38 |

--continued

| Point | Mole Fraction | | |
|---|---|---|---|
| | x | y | z |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

Preferred reaction mixtures are those containing not more than about 0.2 moles of the metals "M" per mole of phosphorous.

In the foregoing expression of the reaction composition, the reactants are normalized with respect to the total of "x", "y" and "z" such that $(x+y+z)=1.00$ mole.

Since the exact nature of the mixed-element APO molecular sieves is not clearly understood at present, although all are believed to contain MO2 tetrahedra in the three-dimensional microporous crystal framework structure, it is advantageous to characterize the mixed-element APO molecular sieves by means of their chemical composition. This is due to the low level of the elements "M" present in certain of the mixed-element APO molecular sieves prepared to date which makes it difficult to ascertain the exact nature of the interaction between the metals "M", aluminum and phosphorous. As a result, although it is believed that $MO_2$ tetrahedra are substituted isomorphously for $AlO_2$ or $PO_2$ tetrahedra, it is appropriate to characterize certain mixed-element APO compositions by reference to their chemical composition in terms of the mole ratios of oxides.

Molecular sieves containing the metals "M", aluminum and phosphorous as framework tetrahedral oxide units are prepared as follows:

Preparative Reagents

Mixed-element APO compositions may be prepared by using numerous reagents. Reagents which may be employed to prepare mixed-element APOs include:
(a) aluminum isopropoxide;
(b) pseudoboehmite or other aluminum oxide;
(c) $H_3PO_4$: 85 weight percent aqueous phosphoric acid;
(d) lithium phosphate or magnesium hydroxide or appropriate salts of the other elements "M", as described above;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

Mixed element APOs may be prepared by forming a starting reaction mixture by mixing aluminum oxide, magnesium hydroxide, lithium phosphate (or the corresponding salts of the other elements "M"). To this mixture the phosphoric acid is added. The resultant mixture is then blended until a homogeneous mixture is observed. To this mixture the templating agent is added and the resulting mixture blended until a homogeneous mixture is observed.

The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

SILICOALUMINOPHOSPHATE MOLECULAR SIEVES

The silicoaluminophosphate molecular sieves are described in U.S. Pat. No. 4,440,871 (incorporated herein by reference), and U.S. Ser. No. 575,745, filed Jan. 31, 1984.

The composite compositions of this invention can be made by the hydrothermal crystallization of reactive gel precursors to the molecular sieve structure in the presence of an electrically conducting or semi-conducting substrate having an inorganic oxide composition layer located in proximity to, preferably, on at least a portion of the surface thereof for crystal growth thereon. The hydrocrystallization conditions for synthesizing the composite compositions are those cited above with respect to the specific molecular sieve composition intended for the phase undergoing hydrothermal crystallization. The molecular sieve gel precursors depend upon the structure being made. Both metals and metals oxides can be utilized in the gel precursors to the molecular sieve framework constituents. In the case of an aluminosilicate based crystal framework, the precursors are the typical aluminate and silicate compositions employed for making such aluminosilicates. In the case of a silica based crystal framework, the precursors are elemental silicon, silicon dioxide in the form of colloidal silica or silica gels or a silicon dioxide layer deposited or formed on the surface of the electrically conducting or semi-conducting substrate. The molecular sieve phase may be made by conventional procedures in the art. It is generally not necessary to employ a new process for generating a molecular sieve phase in the presence of the other phases in order to enjoy the fruits of this invention.

The class of non-zeolitic aluminumophosphate based molecular sieves are typically synthesized by hydrothermal crystallization of reactive aluminum and phosphorus containing gels containing optionally the additional framework elements and an organic template, at temperatures from about 50° C. (122° F) to about 250° C. (482° F.), preferably from about 100° C. (212° F.) to about 225° C. (437° F.). The optimum crystallization temperature depends composition and structure. The $AlPO_4$ and SAPO materials tend not to crystallize at temperatures below about 155° C. (257° F.), whereas several of the MeAPO species crystallize readily at about 100° C. (212° F.).

QAPSO compositions are generally synthesized by hydrothermal crystallizations from a reaction mixture containing active sources of elements(s) "Q" (optional), silicon (optional), aluminum and phosphorus, preferably an organic templating, i.e., structure-directing, agent which is preferably a compound of an element of Group VA of the Periodic Table, and optionally, an alkali or other metal. The reaction mixture is generally placed in a sealed pressure vessel, preferably lined with an inert plastic material such as polytetrafluoroethylene and heated, preferably under autogenous pressure at an effective temperature which is preferably between about 100° C. (212° F.) and about 225° C. (437° F.), more preferably between 100° C. (212° C.) and 200° C. (424° F.), until crystals of the specific variety of QAPSO product are obtained; usually an effective crystallization time of from several hours to several weeks. Generally, effective crystallization times of from about 2 hours to about 30 days are employed with typically from 4 hours to about 20 days being employed to obtain the QAPSO product version. The product is recovered by any convenient method such as centrifugation or filtration.

In synthesizing the QAPSO compositions used in the instant invention, it is preferred to employ a reaction mixture composition expressed in terms of molar ratios as follows:

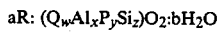

aR: $(Q_wAl_xP_ySi_z)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; "Q" represents at least one element, as hereinbefore described, capable of forming a framework oxide unit, $QO_2^n$, with $SiO_2$, $AlO_2^-$ and $PO_2^+$ tetrahedral oxide units; "n" has a value of $-3$, $-2$, $-1$, 0 or $+1$; and "w", "x", "y", "z" are as defined above.

In the foregoing expression of the reaction composition, the reactants are normalized with respect to the total of "w", "x", "y", and "z" such that $w+x+y+z=1.00$ mole, whereas in the examples in the reaction mixtures may be expressed in terms of molar oxide ratios normalized to the moles of $P_2O_5$. This latter form is readily converted to the former form by routine calculations by dividing the number of moles of each component (including the template and water) by the total number of moles of elements "Q", aluminum, phosphorus and silicon which results in normalized mole fractions based on total moles of the aforementioned components.

In forming reaction mixtures from which the QAPSO molecular sieves are formed, an organic templating agent is preferably employed and may be any of those heretofore proposed for use in the synthesis of conventional zeolite aluminosilicates but, in any case, the template chosen is that template taught in the art for making the particular QAPSO being made. In general, these compounds contain elements of groups VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents may be necessary or useful in producing a particular QAPSO. The initial gel pH in most cases is weakly acidic facilitating the successful incorporation of the hydrolyzable metal cation form of the elements into the frameworks, and inhibiting their precipitation as spurious hydroxides or oxides. Representative templating agents include: quaternary alkylammonium ions such as tetramethylammonium, tetraethylammonium, tetrapropylammonium, tetrabutylammonium, and tetrapentylammonium and amines such as di-n-propylamine, tripropylamine, triethylamine, triethanolamine, piperidine, cyclohexylamine,, 2-methylpyridine, N,N-dimethylbenzylamine, N,N-dimethylethanolamine, choline, N,N'-dimethypiperazine, 1,4-diazabicyclo(2,2,2)octane, N-methyldiethanolamine, N-methylethanolamine, N-methylpiperidine, 3-methylpiperidine, N-methylcyclohexylamine, 3-methylpyridine, 4-methylpyridine, quinuclidine, N,N'-dimethyl1,4-diazabicyclo(2,2,2)octane, di-n-butylamine, neopentylamine, di-n-pentylamine, isopropylamine, t- butylamine, ethylenediamine, diethylenetriamine, triethylenetetraamine, pyrrolidine, 2-imidazolidone, and the like. Not every templating agent will direct the formation of every species of QAPSO, i.e., a single templating agent may, with proper manipulation of the reaction conditions, direct the formation of several QAPSO compositions, and a given QAPSO composition can be produced using several different templating agents.

As Flanigen et al., in a paper entitled, "Aluminophosphate Molecular Sieves and the Periodic Table", published in the "New Developments in Zeolite Science and Technology" Proceedings of the 7th International Zeolite Conference, edited by Y. Murakami, A. Iijima and J. W. Ward, point out:

"The organic template appears to play a critical structure-directing role. The template is trapped or clathrated in the structural voids as the crystals grow. Over eighty five amines and quaternary ammonium species have been used successfully as crystallization templates, including primary, secondary, tertiary and cyclic amines, and alkanolamines. The degree of template-structure specificity varies from the crystallization of $AlPO_45$ with twenty-three templates to the formation of $AlPO_4$-20 with only one template. Table 6, a summary of typical templates forming the major structures, amply illustrates one template forming many structures (11, 31, 41 and 46 with di-n-propylamine). Here, structure control is exercised by other synthesis variables such as temperature, template concentration, gel oxide composition, and pH. The influence of the template is both steric and electronic, and typically exhibits the neat stoichiometry and space-filling characteristics illustrated for $AlPO_4$-5 and 11."

TABLE 6

| Structure-Template Relationships | | | |
|---|---|---|---|
| Structure Type | Typical Template(s) | Structure Type | Typical Template(s) |
| Large Pore | | Small Pore | |
| 5 | tetrapropylammonium, tri-n-propylamine | 14 | isopropylamine |
| 36 | tri-n-propylamine | 17 | quinuclidine, piperidine |
| 37 | tetrapropylammonium + tetramethylammonium | 18 | tetraethylammonium |
|  |  | 34 | tetraethylammonium |
|  |  | 35 | quinuclidine |
| 46 | di-n-propylamine | 44 | cyclohexylamine |
|  |  | 47 | diethylethanolamine |
| Intermediate Pore | | Very Small Pore | |
| 11 | di-n-propylamine di-iso-propylamine | 20 | tetramethylammonium |
| 31 | di-n-propylamine | | |

TABLE 6-continued

| Structure-Template Relationships | | | |
|---|---|---|---|
| Structure Type | Typical Template(s) | Structure Type | Typical Template(s) |
| 41 | di-n-propylamine | | |

The foregoing description of the role of the templating agent is characteristic of the general role of templating agents in respect to the manufacture of the QAPSO family.

The source of silicon may be silicon metal in various shapes and sizes, silica, either as a silica sol or as fumed silica, a reactive solid amorphous precipitated silica, silica gel, alkoxides of silicon, silica containing clays, silicic acid or alkali metal silicates and mixtures thereof.

The most suitable phosphorus source yet found for the aluminophosphates is phosphoric acid, but organic phosphates such as triethyl phosphate have been found satisfactory, and so also have crystalline or amorphous aluminophosphates such as the AlPO4 compositions of U.S. Pat. No. 4,310,440. Organo-phosphorus compounds, such as tetrabutylphosphonium bromide do not appear to serve as reactive sources of phosphorus, but these compounds do function as templating agents. Conventional phosphorus salts such as sodium metaphosphate, may be used, at least in part, as the phosphorus source, but are not preferred.

The preferred aluminum is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, aluminum-containing clays, sodium aluminate and aluminum trichloride, can be employed but are not preferred.

The elements(s) "Q" can be introduced into the reaction system in any form which permits the formation in situ of a reactive form of the element, i.e., reactive to form a framework oxide unit of element "Q". Compounds of element(s) "Q" which may be employed include (but are not limited to) oxides, hydroxides, alkoxides, sulfates, halides, carboxylates and mixtures thereof. Representative compounds which may be employed include inter alia: carboxylates of arsenic and beryllium; cobalt chloride hexahydrate, alpha cobaltous iodide; cobaltous sulfate; cobalt acetate; cobaltous bromide, cobaltous chloride; boron alkoxides; chromium acetate; gallium alkoxides; zinc acetate; zinc bromide; zinc formate; zinc iodide; zinc sulfate heptahydrate; germanium dioxide; iron (II) acetate; lithium acetate; magnesium acetate; magnesium bromide; magnesium chloride; magnesium iodide; magnesium sulfate; manganese acetate; manganese bromide; manganese sulfate; titanium tetrachloride; titanium carboxylates; titanium acetate; zinc acetate; and the like.

After crystallization, the QAPSO product may be isolated and advantageously washed with water and dried in air. The as-synthesized QAPSO generally contains within its internal pore system at least one form of any templating agent employed in its formation. Most commonly, this organic moiety, derived from any organic template, is at least in part present as a charge-balancing cation, as generally is the case with as-synthesized aluminosilicate zeolites prepared from organic-containing reaction systems. It is possible, however, that some or all of the organic moiety may be an occluded molecular species in a particular QAPSO species. As a general rule the templating agent, and hence the occluded organic species, is too large to move freely through the pore system of the QAPSO product and must be removed by calcining the QAPSO at temperatures of 200° C. to 700° C. to thermally degrade the organic species. In some instances the pores of the QAPSO compositions are sufficiently large to permit transport of the templating agent, particularly if the latter is a small molecule, and accordingly complete or partial removal thereof may be accomplished by conventional desorption procedures such as carried out in the case of zeolites. It will be understood that the term "as-synthesized" as used herein does not include the condition of QAPSO species wherein any organic moiety occupying the intracrystalline pore system as a result of the hydrothermal crystallization process has been reduced by post-synthesis treatment such that the value of "m" in the composition formula:

has a value of less than 0.02. The other symbols of the formula are as defined hereinabove. In those preparations in which an alkoxide is employed as the source of elements(s) "Q", aluminum, phosphorous and/or silicon, the corresponding alcohol is necessarily present in the reaction mixture since it is a hydrolysis product of the alkoxide. As has been reported repeatedly in the NZMS patent literature, it has not been determined whether this alcohol participates in the syntheses process as a templating agent. For the purposes of this invention, however, this alcohol is arbitrarily omitted from the class of templating agents, even if it is present in the as-synthesized QAPSO material.

Since the present QAPSO compositions are formed from $AlO_2^-$, $PO_2^+$, $SiO_2$ and $QO_2^n$ framework oxide units which, respectively, has a net charge of $-1$, $+1$, 0 and "n", where "n" is $-3$, $-2$, $-1$, 0 or $+1$, the matter of cation exchangeability is considerably more complicated than in the case of zeolitic molecular sieves in which, ideally, there is a stoichiometric relationship between $AlO_2$ tetrahedra and charge-balancing cations. In the instant compositions, an $AlO_2^-$ tetrahedron can be balanced electrically either by association with a $PO_2$ tetrahedron or a simple cation such as an alkali metal cation or proton, a cation of the element "Q" present in the reaction mixture, or an organic cation derived from the templating agent. Similarly, an $QO_2^n$ oxide can be balanced electrically by association with $PO_2^+$ tetrahedra, a simple cation such as an alkali metal cation, a cation of the metal "Q", organic cations derived from the templating agent, or other divalent or polyvalent metal cations introduced from an extraneous source.

The QAPSO compositions may exhibit cation-exchange capacity when analyzed using ion-exchange techniques heretofore employed with zeolite aluminosilicates and have pore diameters which are inherent in the lattice structure of each species and which are at least about 3 Angstroms in diameter. Dehydration to remove water present in the as-synthesized QAPSO compositions can usually be accomplished, to some degree at least, in the usual manner without removal of the organic moiety, but the absence of the organic species greatly facilitates adsorption and desorption procedures. The QAPSO materials will have various degrees of hydrothermal and thermal stability.

Zeolite structures, used to make the inorganic crystalline composition layer of the composite compositions of this invention, may be generated by the hydrothermal crystallization of an aluminate and silicate under basic conditions. Aqueous gels of the reactants are heated at temperatures ranging from about 50° C. (122° F.) to about 200° C. (392° F.), preferably from about 100° C. (212° F.) to about 175° C. (347° F.). The optimum crystallization temperature depends on composition and structure. A good characterization of processes for the manufacture of zeolites can be found in Chapter Four of Breck, Zeolite Molecular Sieves, Publ. by John Wiley & Sons, New York, N.Y., 1974.

Silica molecular sieves used to make the inorganic crystalline composition layer of the composites of this invention may be generated by hydrothermal crystallization treatment of aqueous gel precursors or of aqueous solutions containing a sacrificial source of silicon. A good characterization of a process for the manufacture of silica molecular sieves, e.g., silicalite, can be found in U.S. Patent 4,061,724. A good characterization of a process for the preparation of crystalline silica polymorphs, e.g., silicalite, using elemental silicon as the silicon sources can be found in European Patent Application No. 0 137 289, published Apr. 17, 1985.

In the hydrothermal crystallization treatment of aqueous gel precursors to silica molecular sieves, for example, a silica coated silicon wafer can be immersed in a gel precursor containing a silica source, a structure directing template such as TPAOH and water under basic conditions. The growth of fluoride silicalite requires, in addition to the above-mentioned components, the presence of fluoride and can be carried out under acidic conditions. The aqueous gel precursor solutions are heated at temperatures in the range of about 50° C. (122° F.) to about 200° C. (392° F.), preferably in the range of about 100° C. (212° F.) to about 175° C. (347° F.). The optimum crystallization temperature depends on composition and structure.

In the hydrothermal crystallization treatment of aqueous solutions containing a sacrificial source of silicon, for example, a silica coated silicon wafer and a silicon metal source can be immersed in an aqueous solution containing a structure directing template such as TPAOH and a surfactant such as ethanol under basic conditions. The reaction time and temperature are not critical so long as sufficient time at elevated temperature is provided to allow the reaction of the silicon and the formation of the silica molecular sieve. The reaction temperature in general can vary in the range of about 100° C. to about 300° C., preferably in the range of about 140° C. to about 200° C. The reaction time can be as long as practical, preferably in the range of from about 30 hours to about 300 hours. For purposes of this invention, the ratio of silicon (sacrificial silicon only) to water should be at most about 1:1000, preferably at most about 1:5,000, in order to grow silicalite at desired layer thickness. The optimum crystallization temperature and reaction time depend on composition and structure.

Crystalline molecular sieves, whether zeolites or silica or of the NZMS variety, are usually formed as small crystals of a size in the range of about 0.01 micron ($0.4 \times 10^{-6}$ inch) as the shortest crystal dimension to about 150 microns in the longest crystal dimension (0.006 inch) Crystalline molecular sieves are not spheres, they can range from regularly to irregularly shaped structures in the fashion of most crystals. Many are formed as part of agglomerations of crystals.

As referred to hereinabove, a sacrificial source of an inorganic crystalline framework metal can be utilized in the process of this invention. For example, in the preparation of a silicalite inorganic crystalline composition layer as described above, the source of the inorganic crystalline framework silicon can be elemental silicon in the form of powders, wafers, rods, pellets and the like or silicon dioxide in the form of colloidal silica or silica gels. Other inorganic crystalline framework metals may also be used as sacrificial sources in the process of this invention. The sacrificial sources of inorganic crystalline framework metal can prevent or reduce any deterioration or damage during crystallization to the electrically conducting or semi-conducting substrate having an inorganic oxide composition layer upon at least a portion of the surface thereof.

As described hereinabove, a surface active agent or surfactant can be utilized in the process of this invention. The surfactant can typically be added to the template solution prior to digestion thereof. In a preferred embodiment of this invention, a surfactant is used in those processes employing a sacrificial source of an inorganic crystalline framework metal. Illustrative surfactants include ethanol, dimethyldodecylamine and the like. The amount of surfactant is not narrowly critical and can vary over a wide range.

As described above, the composite compositions of this invention are conveniently formed by the hydrothermal crystallization of the inorganic crystalline composition phase in the presence of the electrically conducting or semi-conducting substrate having an inorganic oxide composition layer located in proximity to, preferably on, at least a portion of the surface thereof. Broadly speaking, the inorganic crystalline composition phase of the composite compositions is derived by the hydrothermal crystallization of the components thereof from an aqueous gel. The composite compositions derive from the hydrothermal crystallization of the precursor gel to the formation of an intended inorganic crystalline composition phase in the presence of the electrically conducting or semi-conducting substrate having an inorganic oxide composition layer upon at least a portion of the surface thereof which constitute the other phases of the composite compositions.

The electrically conducting or semi-conducting substrate provides a support for the inorganic oxide composition phase (middle layer) which in turn provides for crystal growth. As an embodiment of this invention and in accordance with the teachings of copending U.S. patent application Ser. No. 058,259, filed June 4, 1987, once one inorganic crystalline phase is crystallized in the presence of the electrically conducting or semi-conducting substrate, the composite may be used as the support for the creation of still another solid inorganic crystalline phase. This procedure may be repeated as many times as desired or as there exists enough molecular sieves of different compositions but having the same crystalline framework to provide a composite composition having an inorganic crystalline composition phase of an essentially single crystal structure. By this technique, one may produce a composite composition having repeated layers of different molecular sieves in an onion skin pattern, except the skins are chemically bonded to one another. There are occasions where one might wish to blend the ingredients of distinct molecular sieve compositions and effect the hydrothermal differential crystallization to form a mixed phase composition. In the typical case, the composite compositions will be formed by the hydrothermal crystallization of a molecular sieve reaction mixture in contact with another already formed or partially formed crystalline molecular sieve of appropriate crystalline structure.

It is believed that the inorganic crystalline phase of the composite compositions is formed by the growth of a crystal onto the surface of the inorganic oxide composition layer. It may be the case in some instances that this growth is facilitated by the deposition substrate. Such may be termed a "seeding" effect. The growth in this manner yields a layer of crystalline molecular sieve deposited on a substrate surface which grafts in the process of the hydrothermal crystallization to the inorganic oxide crystal framework of the substrate surface. In this fashion, one may obtain an electrically conducting or semi-conducting substrate having an inorganic oxide composition layer upon at least a portion of the surface thereof and surrounded or enveloped by a layer or a film or a mantle of the molecular sieve(s) phase.

The shape of the composite composition is determined by the shape of the electrically conducting or semi-conducting substrate. The configuration of the composite of the invention is not critical to this invention, but can be important in respect to a particular use.

The present moisture sensing elements are electrically continuous. The preferred method for preparing an electrically continuous composite composition-containing article for use in the present sensing elements is to grow molecular sieves directly onto a thin inorganic oxide coating of a conductor or semiconductor as discussed herein and in U.S. patent application Ser. No. 213,261, filed June 29, 1988. This method results in a layer which is electrically continuous because the crystallization on the surface takes the form of interlocking crystalline aggregates. The crystalline intergrowths minimize the grain boundary effects noted in powders. The electrically continuous composite composition containing article is then equipped with one or more electrodes to form a moisture sensing element. The article is preferably prepared in such a fashion so as to increase sensitivity and reduce response time. Thus, the article should be thick enough so that sufficient pore volume is available that enough water may be adsorbed to change the resistance and/or capacitance and/or impedance but not so thick as to inhibit diffusion of water into and out of the article. The article may be configured in any suitable shape provided it functions as described herein.

The impedance may be measured directly or the measurement may be carried out indirectly by incorporating the moisture sensing element in a feedback circuit of an oscillator such that the oscillator frequency varies with moisture content. Moisture content may then be determined using an electronic counter. The signal thus produced may be used to modulate a radio signal and thereby be transmitted over a distance.

The electrode or electrodes may be any suitable conductive material, preferably metal, which is substantially not affected by the environment being analyzed. They may be affixed or attached using conventional procedures, such as screen printing, sputtering and the like. They may be situated to form a parallel plate or a coplanar configuration. In the parallel plate configuration, electrodes are placed in association with substantially opposing, preferably parallel, surfaces of the article. The conducting or semiconducting substrate may act as one of the electrodes and therefore only one electrode is required in the parallel plate configuration. In the coplanar configuration, two electrodes are placed at different locations in association with the same surface of the article. The electrode or electrodes (other than the substrate) are preferably porous. Porosity may be achieved by utilizing a screen, by sputtering in such a fashion as to give porous electrodes or by mechanically removing some of the electrode following deposition to decrease electrode surface area while retaining electrical continuity. It is not necessary, although preferable, that the electrodes be porous as long as sufficient inorganic crystalline composition surface area remains exposed to the fluid stream so as not to disturb diffusion. The electrodes may be in the form of nonporous circles or squares as long as their surface area does not impede diffusion. They may also be in the form of nonporous interdigitated electrodes. In addition, these electrodes may be made porous by mechanical means following deposition. The electrodes should be sufficiently large so that sensitivity and measurement frequency are effectively provided for, but not so large that diffusion of the adsorbing species and therefore response time is limited.

To realize maximum utility as a moisture sensing element, it must respond rapidly to changes in the surrounding water vapor pressure. For a $\frac{1}{4}$-inch diameter by $\frac{1}{4}$-inch long article the response time at high water vapor pressures is measurable in seconds; the response time at extremely low water vapor pressures is measurable in minutes. A faster response may be achieved by reducing the volume of the article, and by increasing the exposed surface of the article.

The electrical properties of the article are more affected by polar than by non-polar adsorbates. Normal atmospheric constituents, other than water, however, show nonappreciable effect on such properties. Nonpolar materials will ordinarily affect such properties slightly, but their effect on the water loading capability of the inorganic crystalline compositions must be considered. In any case, proper calibration, if the concentration of the interfering material is known, can overcome this difficulty. For example, the rapid determination of the water content of organic liquids such as ethanol or hexane is feasible provided that the sensing element is calibrated with a series of samples of known water content and the medium is not otherwise contaminated. In these cases, alternatively, the sensing element can be made of an inorganic crystalline composition which is of such a pore size that it will not absorb the organic liquid.

Being ionic conductors, crystalline zeolites are subject to polarization by direct current. The rate of polarization has been shown to be slow, however, so that a pulsed direct current resistance measuring circuit is feasible. Difficulties with polarization are best overcome by using an alternate current (A.C.) measuring circuit. With all the presently useful inorganic crystalline compositions, it is preferred to use an A.C. measuring circuit.

In many instances, the change in electrical impedance due to temperature varies substantially linearly. Thus, in these situations, compensating for temperature is relatively easy. In any event, the change in impedance due to temperature can be compensated for by employing an identical element hermetically sealed, by use of any of the temperature-controlling methods commonly employed with electronic measuring devices or by actual calibration over a range of temperatures.

DETAILED DESCRIPTION OF THE DRAWINGS

Figure 1:
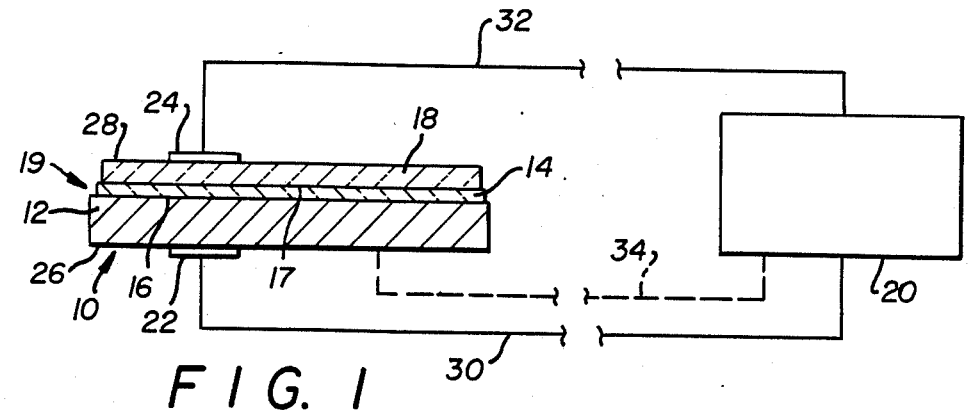
FIG. 1 is a schematic illustration, partly in cross-section, showing one embodiment of the present invention in a parallel plate configuration.

FIG. 1 schematically illustrates a humidity sensor, shown generally at 10, which includes a silicon wafer 12, a silica layer 14 deposited on and contiguous to the top surface 16 of silicon wafer 12, a silicalite layer 18 grown on and contiguous to top surface 17 of silica layer 14, and an impedance analyzer 20. Gold electrodes 22 and 24 are attached, e.g., by screen printing or sputtering, to the bottom surface 26 of silicon wafer 12 and the top surface of 28 silicalite layer 18, respectively.

Electrode 24 may be impervious to moisture so long as it does not cover a relatively large portion, in particular substantially all of top surface 28 of silicalite layer 18. However, it is preferred that electrode 24 be porous. Such porosity can be achieved by utilizing screen printing, by sputtering or by mechanically removing some of the electrode following deposition to decrease electrode surface area while retaining electrical continuity. Electrode 24 is suitably sized to be large enough to provide acceptable sensitivity and measurement frequency, but not so large that diffusion in and out of silicalite layer 18, and therefore response time, is unduly restricted or limited.

Teflon coated wire leads 30 and 32 are attached using silver paint, to electrodes 22 and 24, respectively. The wire leads 30 and 32 are also connected to impedance analyzer 20 so that as an alternating electric current is passed between electrodes 22 and 24 through silicon wafer 12, silica layer 14 and silicalite layer 18, the impedance of this composite composition 19 (silicon wafer 12, silica layer 14 and silicalite layer 18) can be measured by impedance analyzer 20. A particularly useful instrument as the impedance analyzer 20 is a Hewlett-Packard 4192 A AC impedance analyzer.

One useful alternative involves an embodiment with only one electrode, such as electrode 24, attached to silicalite layer 18. In this embodiment, silicon wafer 12 acts as the second electrode and a wire lead 34, illustrated in shadow in FIG. 1, is attached directly to silicon wafer 12 and can be connected to impedance analyzer 20. Except as expressly described herein, this alternate embodiment is structured and functions in a manner similar to humidity sensor 10.

The relative thickness of silicon wafer 12, silica layer, 14 and silicalite layer 18 is selected to provide for effective and efficient humidity sensing. For example, the thickness of silica layer 14 is sufficiently large to provide for effective growing of silicalite layer 18 without being so large as to interfere with the sensitivity of the humidity measurements. On the other hand, silicalite layer 18 is sufficiently thick to provide the desired sensitivity in humidity measurements without being so thick as to unduly restrict or limit the response time (the time before the composite 19 reaches equilibrium with the environment the humidity of which is to be measured) of humidity sensor 10. For example, silicon wafer 12 may be about 5 mils thick, silica layer 14 may be about 1 micron thick and silicalite layer 18 may be about 50 microns thick.

Humidity sensor 10 functions as follows. Composite composition 19, along with electrodes 22 and 24 and attached wire leads 30 and 32, is placed in a gaseous environment the humidity of which is to be determined. The wire leads 30 and 32 are connected to impedance analyzer 20, as described above. After a period of time, e.g., on the order of 20 minutes, substantial adsorption equilibrium between the composite composition 19 and the surrounding environment is achieved. At this point, impedance analyzer 20 is caused to pass a controlled alternating current between electrodes 22 and 24 through composite composition 19 and to measure the impedance of composite composition 19 at the humidity conditions present in the environment surrounding composite composition 19. It should be noted that the impedance can be measured directly and/or through conventional frequency modulation, as described elsewhere herein. This impedance measurement is related to the concentration (e.g., partial pressure) of water in this environment. Humidity sensor 10 can be calibrated in advance to provide a humidity/impedance relationship or curve. Thus, by knowing the impedance of composite composition 19, one can easily determine the humidity, i.e., the water concentration, of the surrounding environment.

Figure 2:
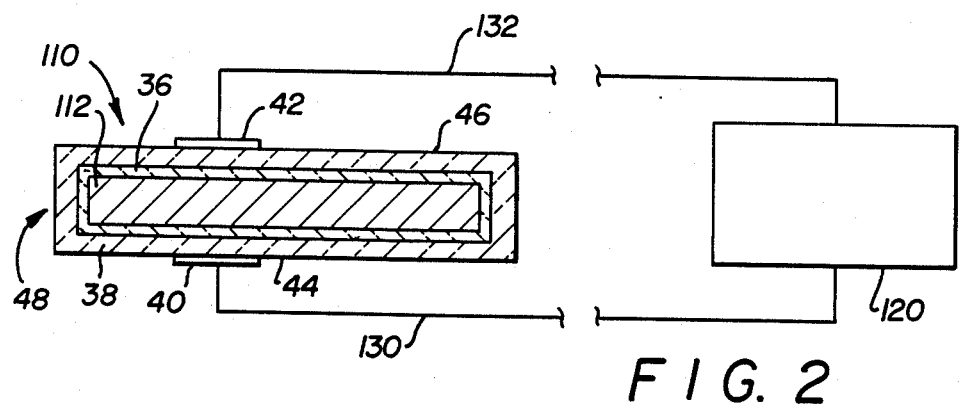
FIG. 2 is a schematic illustration, partly in cross-section, showing another embodiment of the present invention in a parallel plate configuration.

The embodiment schematically illustrated in FIG. 2 is, except as expressly described below, structured and functions similarly to the embodiment illustrated in FIG. 1. The principal differences between the two embodiments are in the composite configuration and in the placement of the electrodes. Components in FIG. 2 which correspond to components in FIG. 1 are indicated by the same reference numeral increased by 100.

In FIG. 2, humidity sensor 110 includes a silicon wafer 112 which is coated on both sides by silica coating 36 which, in turn, is coated on both sides by silicalite coating 38. Two gold electrodes 40 and 42 are affixed to the bottom surface 44 and the top surface 46, respectively, of silicalite coating 38. Wire leads 130 and 132 connect electrodes 40 and 42, respectively, to impedance analyzer 120. The combination of silicon wafer 112, silica layer 36 and silicalite layer 38 is referred to as composite composition 48.

Electrodes 40 and 42 are configured and sized based on criteria similar to those, described above, used to configure and size electrode 24. Preferably, electrodes 40 and 44 are porous.

Composite composition 48 may be prepared by growing silicalite layer 38 onto silicon wafer 112 which previously has been coated with silica coating 36. The thickness of silica coating 36 and silicalite coating 38 are based on criteria similar to those, described above, used to set the thickness of silica layer 14 and silicalite layer 18, respectively. For example, silica coating 36 may be about 1 micron thick and silicalite coating 38 may be about 50 microns thick. Silicon wafer 112, like silicon wafer 12, may be about 5 mils thick.

Humidity sensor 110 functions in a manner substantially similar and analogous to that described above with respect to humidity sensor 10.

Figure 3:
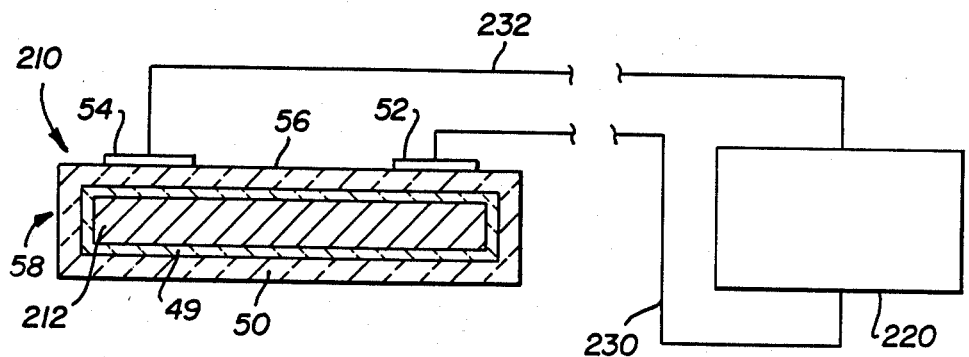
FIG. 3 is a schematic illustration, partly in cross section, showing a further embodiment of the present invention in a coplanar configuration.

The embodiment schematically illustrated in FIG. 3 is, except as expressly described below, structured and functions similarly to the embodiment illustrated in FIG. 1. The principal differences between the two embodiments are in the composite configuration and in the placement of the electrodes. Components in FIG. 3 which correspond to components in FIG. 1 are indicated by the same reference numeral increased by 200.

In FIG. 3, humidity sensor 210 includes a silicon wafer 212 which is coated on both sides by silica coating 49 which, in turn, is coated on both sides by silicalite coating 50. Two gold electrodes 52 and 54 are affixed to different locations on the top surface 56 of silicalite coating 50. Wire leads 230 and 232 connect electrodes 52 and 54, respectively, to impedance analyzer 220. The combination of silicon wafer 212, silica layer 49 and silicalite layer 50 is referred to as composite composition 58. Humidity sensor 210 is substantially similar to humidity sensor 110 except the placement of the electrodes. In humidity sensor 110 the electrodes are placed in a parallel plate mode, while in humidity sensor 210 the electrodes are placed in a coplanar mode.

Electrodes 52 and 54 are configured and sized based on criteria similar to those, described above, used to configure and size electrode 24. Preferably electrodes 52 and 54 are porous.

Composite composition 58 may be prepared by growing silicalite layer 50 onto silicon wafer 212 which previously has been coated with silica coating 49. The thickness of silica coating 49 and silicalite coating 50 are based on criteria similar to those, described above, used to set the thickness of silica layer 14 and silicalite layer 18, respectively. For example, silica coating 49 may be about 0.001 microns thick and silicate coating 50 may be about 50 microns thick. Silicon wafer 12, like silicon wafer 12, may be about 5 mils thick.

Humidity sensor 210 functions in a manner substantially similar and analogous to that described above with respect to humidity sensor 10.

The following non-limiting examples further illustrate certain aspects of the present invention.

EXAMPLE 1

A solution was prepared by combining 5.0 grams of an aqueous 40wt % tetrapropylammonium hydroxide (TPAOH) solution, 2.0 grams of absolute ethanol and 93 grams of water, and stirring until well mixed. 15 grams of this solution was added to the Teflon liner of a Parr acid digestion vessel followed by 0.0002 grams of −200 mesh silicon metal powder and a silica coated silicon wafer. The relative composition of the reaction mixture was 104 $TPA_2O$, 1.0 $SiO_2$, and 112,000 $H_2O$. The digestion vessel was sealed and heated at 175° C. for 96 hours. The wafer was removed from the reaction vessel and washed with a stream of water for one minute. The wafer was covered on both sides with a dense crystalline layer. Scanning electron microscopy of the wafer showed that the crystallites were oriented such that they pointed up from the wafer surface with the longest crystalline axis perpendicular to the wafer surface. This sample was calcined at 600° C. for two hours to remove the organic material contained in the pore volume and to allow improved water adsorption. The dense crystalline layer was determined to be silicalite.

Gold electrodes were sputtered onto this coated wafer in the parallel plate format, described above. These electrodes were connected to wire leads and a Hewlett Packard 4192A AC impedance analyzer to provide a humidity sensor similar in Configuration to humidity sensor 110 of FIG. 2, described above.

The coated wafer and electrodes were placed in a sample cell, i.e., a volume in which the humidity can be controlled, for testing.

The temperature of the sample cell was controlled by an Omega CN2011 Programmable Temperature Controller. Fluid streams containing a known amount of water for inclusion in the sample cell were generated in one of several ways: for generation of streams containing ppm or lower levels of entrained water a Kintek 570-C Precision Gas Standards Generator was used and the level of entrained water confirmed with a DuPont 5700 Moisture Analyzer; for generation of streams with entrained moisture levels between 11.5% and 97% relative humidity nitrogen was bubbled through saturated aqueous salt solutions of known water vapor pressure; and 100% relative humidity streams were prepared by bubbling nitrogen through water. Previous experiments showed that the resistance and/or capacitance and/or impedance of the present humidity sensors was not sensitive to the presence of nitrogen or oxygen gas.

The impedance of this humidity sensor was tested at 1 kHz and 25° C. with varying relative humidity. Results were as follows:

| Relative Humidity | Impedance, M ohms |
| --- | --- |
| 0 | 1.25 |
| 12 | 1.16 |
| 33 | 1.00 |
| 52 | 0.76 |
| 68 | 0.56 |
| 87 | 0.30 |
| 100 | 0.066 |

In addition, the impedance of this humidity sensor was tested at 10 kHz at 52% relative humidity with varying temperature. Results were as follows:

| Temperature, °C. | Impedance, M ohms |
| --- | --- |
| 23 | 0.093 |
| 40 | 0.112 |
| 60 | 0.117 |
| 80 | 0.119 |
| 100 | 0.121 |

Both of these relationships demonstrate the usefulness of the humidity sensor prepared as described above.

EXAMPLE 2

A solution was prepared by combining 2.0 grams of an aqueous 40wt % tetrapropylammonium hydroxide (TPAOH) solution, 4.0 grams of absolute ethanol and 194 grams of water and stirring until well mixed. 15 grams of this solution was added to the Teflon liner of a Parr acid digestion vessel followed by .0002 grams of +200 mesh silicon metal and a silica coated silicon wafer. The relative composition of this reaction mixture was 21 $TPA_2O$, 1.0 $SiO_2$, and 112,000 $H_2O$. The digestion vessel was sealed and heated at 150° C. for 18 days. The wafer was removed from the reaction vessel and washed with a stream of water for one minute. The wafer was covered on both sides with a dense crystalline layer. Scanning electron microscopy of the wafer showed that the crystallites were oriented such that they lay flat on the surface. This sample was not calcined to remove the organic material in the pore volume. The dense crystalline layer was determined to be silicalite.

Gold electrodes were sputtered onto this coated wafer in the parallel plate format, described above. These electrodes were connected to wire leads and a Hewlett Packard 4192A AC impedance analyzer to provide a humidity sensor similar in configuration to humidity sensor 110 of FIG. 2, described above.

The coated wafer and electrodes were placed in the sample cell, i.e., a volume in which the humidity can be controlled, for testing.

The impedance of this humidity sensor was tested at various relative humidities and was found to vary in a reversible and reproducible fashion when the humidity level was varied between ambient humidity and 100% relative humidity. Thus, this device is useful as a humidity sensor.

EXAMPLE 3

A humidity sensor was prepared and tested as in Example 2, except that the coated wafer was calcined at 600° C. before the electrodes were sputtered on. This humidity sensor exhibited similar reversibility and reproducibility of impedance response as did the humidity sensor of Example 2, and improved sensitivity (relative to the Example 2 sensor). This improved sensitivity (or improved response time) appears to be a result of the calcination of the coated wafer which removed organic material filling the interior pore volume. The improved response time of this humidity sensor was demonstrated by the attainment of equilibrium within 14 seconds after changing from ambient humidity to 100% relative humidity.

While this invention has been described with respect to various specific examples and embodiments, it is to be understood that the invention is not limited thereto and that it can be variously practiced within the scope of the following claims.

What is claimed is:

1. A moisture sensing element comprising an electrically continuous article comprising a multi-compositional, multi-phase composite composition comprising as phases thereof (i) an electrically conducting or semiconducting substrate, (ii) an inorganic oxide composition layer in proximity to at least a portion of the surface of said electrically conducting or semiconducting substrate and (iii) an inorganic crystalline molecular sieve composition layer upon at least a portion of the surface of said inorganic oxide composition layer, wherein the different phases of the composite composition are substantially contiguous and exhibit at least one of a distinct compositional heterogeneity and a distinct structural heterogeneity of one phase to the other; and at least one electrode affixed to said article in current carrying relationship so that the current carried by said electrode passes through at least a portion of said inorganic molecular sieve crystalline composition layer.

2. The element of claim 1 wherein said inorganic crystalline molecular sieve composition layer is grown by crystal growth upon at least a portion of the surface of said inorganic crystalline composition layer.

3. The element of claim 1 wherein said electrically conducting or semi-conducting substrate has a minimum conductivity or at least about $10^{-9}$ ohm$^{-1}$ cm$^{-1}$.

4. The element of claim 1 wherein said electrical conducting or semi-conducting substrate contains a material selected from the group consisting of silicon, aluminum, copper, gold, silver, platinum, gallium, molybdenum, gallium arsenide, gallium phosphide and mixtures thereof.

5. The element of claim 1 wherein said electrically conducting or semi-conducting substrate is a wafer, fiber, optical fiber, pill, extrusion or pellet.

6. The element of claim 1 wherein said electrically conducting or semi-conducting substrate has an etched or lithographed surface.

7. The element of claim 1 wherein said inorganic oxide composition layer is an oxide selected from the group consisting of silica, alumina, titania, germania, zirconia, magnesia, gallia and mixtures thereof.

8. The element of claim 1 wherein said inorganic oxide composition layer has a thickness in the range of about 0.001 micron to about 100 microns.

9. The element of claim 1 wherein said inorganic oxide composition layer is not of a thickness to be sufficiently insulating so as to inhibit an electrically change in said inorganic crystalline composition layer from affecting charge carrying species of said electrical conducting or semi-conducting substrate.

10. The element of claim 1 wherein said inorganic crystalline molecular sieve composition layer is a molecular sieve selected from the group consisting of zeolitic molecular sieves, silica molecular sieves or nonzeolitic molecular sieves and mixtures thereof.

11. The element of claim 10 wherein said molecular sieve includes at least one organic templating agent.

12. The element of claim 10 wherein said molecular sieve is substantially free of organic templating agent.

13. The element of claim 10 wherein said molecular sieve is selected from the group consisting of an A-type zeolitic molecular sieves, X-type zeolitic molecular sieves, Y-type zeolitic molecular sieves, L-type zeolitic molecular sieves, F-type zeolitic molecular sieves, W-type zeolitic molecular sieves, LZ-202, LZ-105 and mixtures thereof.

14. The element of claim 10 wherein the molecular sieve is selected form the group consisting of ZSM-5, ZSM-11, ZSM-12, ZSM-20, ZSM-34, omega zeolite, beta zeolite and mixtures thereof.

15. The element of claim 10 wherein said molecular sieve is a silica molecular sieve selected from the group consisting of silicalite, silicalite II, fluoride silicalite and mixtures thereof.

16. The element of claim 10 wherein said molecular sieve is a non-zeolitic molecular sieve having an empirical chemical composition on an anhydrous basis expressed by the formula I:

$$mR(Q_wAl_xP_ySi_z)O_2 \qquad (I)$$

where
"Q" represents
(a) at least one element present as a framework oxide unit "QO$_2$n" with charge "n" where "n" may be $-3, -2, -1, 0$ or $+1$;
 (i) a mean "T—O" distance in tetrahedral oxide structure between about 1.51 Å and about 2.06 Å
 (ii) a cation electronegativity between about 125 kcal/gm-atom to about 310 kcal/gm-atom and
 (iii) the capability of forming stable Q—O—P, Q—O—Al or Q—O—Q bonds in crystalline three dimensional oxide structures having a "Q—" bond dissociation energy greater than about 59 kcal/gm-atom at 298° K.;
"R" represents at least one organic templating agent present in the intracrystalline pore system;

"m" represents the molar amount of "R" present per mole of $(Q_wAl_xP_ySi_z)O_2$ and has a value from zero to about 0.3; and ,"w", "x", "y" and "z" represent the mole fractions of $QO_2{}^n$, $AlO_2-$, $PO_2+$, $SiO_2$, respectfully, present as framework oxide units; and the mole fractions of "Q"; aluminum, phosphorus and silicon, respectively, present as framework oxides said mole fractions being within the following limiting compositional values:

w is equal to 0 to 98 mole percent;
y is equal to 1 to 99 mole percent;
x is equal to 1 to 99 mole percent, and
z is equal to 0 to 98 mole percent.

17. The element of claim 16 wherein said non-zeolitic molecular sieve is selected from the group consisting of $AlPO_4$, SAPO, MeAPO, MeAPSO, ELAPO and ELAPSO molecular sieves and mixtures thereof.

18. The element of claim 1 wherein said inorganic crystalline molecular sieve composition layer has a thickness in the range of about 500 Å to about 100 microns.

19. The element of claim 1 wherein said inorganic crystalline molecular sieve composition layer is of sufficient thickness so that an electrical change in the inorganic crystalline composition layer affects charge carrying species of the electrically conducting or semi-conducting substrate.

20. The element of claim 1 wherein said composite composition comprises (i) a silicon or aluminum substrate and (ii) a silicon dioxide of aluminum oxide layer upon at least a portion of the surface of said silicon or aluminum substrate.

21. The element of claim 20 wherein said molecular sieve is selected from the group consisting of zeolitic molecular sieves, silica molecular sieves, non-zeolitic molecular sieves and mixtures thereof.

22. The element of claim 1 wherein said article has at least two substantially opposing surfaces and one of said electrodes is located in association with each of said substantially opposing surfaces.

23. The element of claim 1 wherein said article has a substantially planar surface -on said inorganic crystalline composition layer and two of said electrodes are located in association with said substantially planar surface.

24. The element of claim 1 wherein said electrodes are made of metal.

25. The element of claim 1 wherein at least one of said electrodes is porous.

26. The element of claim 1 wherein all of said electrodes are porous.

27. A hydrometer comprising an electrically continuous moisture sensing hydrometer comprising a multicompositional, multi-phase composite composition comprising as phases thereof (i) an electrically conducting or semi-conducting substrate, (ii) an inorganic oxide composition layer in proximity to at least a portion of the surface of said electrically conducting or semi-conducting substrate and (iii) an inorganic crystalline molecular sieve composition layer upon at least a portion of the surface of said inorganic oxide composition layer, wherein the different phases of the composite composition are substantially contiguous and exhibit at least one of a distinct compositional heterogeneity and a distinct structural heterogeneity of one phase to the other; at least one electrode affixed to said article in current carrying relationship so that the current carried by said electrode passes through at least a portion of said inorganic crystalline molecular sieve composition layer ; and an impedance measuring means connected to said electrode and said substrate or to a plurality of said electrodes for measuring the electrical impedance of at least a portion of said composite composition.

28. The hydrometer of claim 27 wherein said inorganic crystalline molecular sieve composition layer is grown by crystal growth upon at least a portion of the surface of said inorganic oxide composition layer.

29. The hydrometer of claim 27 wherein said electrically conducting or semi-conducting substrate has a minimum conductivity or at least about $10^{-9}$ ohm$^{-1}$ cm$^{-1}$.

30. The hydrometer of claim 27 wherein said electrically conducting or semi-conducting substrate contains silicon, aluminum, copper, gold, silver, platinum, gallium, molybdenum, gallium arsenide, gallium phosphide and mixtures thereof.

31. The hydrometer of claim 27 wherein said electrically conducting or semi-conducting substrate is a wafer, fiber, optical fiber, pill, extrusion or pellet.

32. The hydrometer of claim 27 wherein said electrically conducting or semi-conducting substrate has an etched or lithographed surface.

33. The hydrometer of claim 27 wherein said inorganic oxide composition layer is an oxide selected from the group consisting of silica, alumina, titania, germania, zirconia, magnesia, gallia and mixtures thereof.

34. The hydrometer of claim 27 wherein said inorganic oxide composition layer has a thickness in the range of about 0.001 microns to about 100 microns.

35. The hydrometer of claim 27 wherein said inorganic oxide composition layer is not of a thickness to be sufficiently insulating so as to inhibit an electrical change in said inorganic crystalline composition layer from affecting charge carrying species of said electrically conducting or semi-conducting substrate.

36. The hydrometer of claim 27 wherein said inorganic crystalline composition layer is a molecular sieve selected from the group consisting of zeolitic molecular sieves, silica molecular sieves or non-zeolitic molecular sieves and mixtures thereof.

37. The hydrometer of claim 36 wherein said molecular sieve includes at least one organic templating agent.

38. The hydrometer of claim 36 wherein said molecular sieve is substantially free of organic templating agent.

39. The hydrometer of claim 36 wherein said molecular sieve is selected from the group consisting of an A-type zeolitic molecular sieves, X-type zeolitic molecular sieves, Y-type zeolitic molecular sieves, L-type zeolitic molecular sieves, F-type zeolitic molecular sieves, W-type zeolitic molecular sieves, LZ-202, LZ-105 and mixtures thereof.

40. The hydrometer of claim 36 wherein the molecular sieve is selected form the group consisting of ZSM-5, ZSM-11, ZSM-12, ZSM-20, ZSM-34, omega zeolite, beta zeolite and mixtures thereof.

41. The hydrometer of claim 36 wherein said molecular sieve is a silica molecular sieve selected from the group consisting of silicalite, silicalite II, fluoride silicalite and mixtures thereof.

42. The hydrometer of claim 36 wherein said molecular sieve is a non-zeolitic molecular sieve having an empirical chemical composition on an anhydrous basis expressed by the formula I:

$$mR(Q_wAl_xP_ySi_z)O_2 \quad (I)$$

where

"Q" represents
(a) at least one element present as a framework oxide unit "$QO_2^n$" with charge "n" where "n" may be $-3, -2, -1, 0$ or $+1$;
  (i) a mean "T-O" distance in tetrahedral oxide structure between about 1.51 Å and about 2.06 Å
  (ii) a cation electronegativity between about 125 kcal/gm-atom to about 310 kcal/gm-atom and
  (iii) the capability of forming stable Q—O—P, Q—O—Al or Q—)—Q bonds in crystalline three dimensional oxide structures having a "Q—O" bond dissociation energy greater than about 59 kcal/gm-atom at 298° K.;

"R" represents at least one organic templating agent present in the intracrystalline pore system;

"m" represents the molar amount of "R" present per mole of $(Q_wAl_xP_ySi_z)O_2$ and has a value from zero to about 0.3; and "w", "x", "y" and "z" represent the mole fractions of $QO_2^n$, $AlO_2-$, $PO_2+$, $SiO_2$, respectfully, present as framework oxide units; and the mole fractions of "Q"; aluminum, phosphorus and silicon, respectively, present as framework oxides said mole fractions being within the following limiting compositional values:

w is equal to 0 to 98 mole percent;
y is equal to 1 to 99 mole percent;
x is equal to 1 to 99 mole percent, and
z is equal to 0 to 98 mole percent.

43. The hydrometer of claim 42 wherein said non-zeolitic molecular sieve is selected from the group consisting of AlPO$_4$, SAPO, MeAPO, MeAPSO, ELAPO and ELAPSO molecular sieves and mixtures thereof.

44. The hydrometer of claim 27 wherein said inorganic crystalline molecular sieve composition layer has a thickness in the range of about 500 Å to about 100 microns.

45. The hydrometer of claim 27 wherein said inorganic crystalline molecular composition layer is of sufficient thickness so that an electrical change in the inorganic crystalline composition layer affects charge carrying species of the electrically conducting or semi-conducting substrate.

46. The hydrometer of claim 27 wherein said composite composition comprises (i) a silicon or aluminum substrate and (ii) a silicon dioxide of aluminum oxide layer upon at least a portion of the surface of said silicon or aluminum substrate.

47. The hydrometer of claim 46 wherein said molecular sieve is selected from the group consisting of zeolitic molecular sieves, silica molecular sieves, non-zeolitic molecular sieves and mixtures thereof.

48. A method for measuring the water content of a fluid system which comprises immersing in said fluid system an electrically continuous sensing element comprising a multi-compositional, multi-phase composite composition comprising as phases thereof (i) an electrically conducting or semi-conducting substrate, (ii) an inorganic oxide composition layer in proximity to at least a portion of the surface of said electrically conducting or semi-conducting substrate and (iii) an inorganic crystalline molecular sieve composition layer upon at least a portion of the surface of said inorganic oxide composition layer, wherein the different phases of the composite composition are substantially contiguous and exhibit at least one of a distinct compositional heterogeneity and a distinct structural heterogeneity of one phase to the other; and measuring the electrical impedance of at least a portion of said sensing element, said electrical impedance being correlatable to the moisture content in said fluid system.

49. The method of claim 48 wherein said measuring occurs after said fluid system and said sensing element have reached substantial adsorption equilibrium.

50. The method of claim 48 wherein said measuring includes passing an alternating current through at least a portion of said sensing element.

51. The method of claim 48 wherein said inorganic crystalline molecular sieve composition layer is grown by crystal growth upon at least a portion of the surface of said inorganic crystalline composition layer.

52. The method of claim 48 wherein said electrically conducting or semi-conducting substrate has a minimum conductivity of at least about $10^{-9}$ ohm$^{-1}$cm$^{-1}$.

53. The method of claim 48 wherein said electrically conducting or semi-conducting substrate contains silicon, aluminum, copper, gold, silver, platinum, gallium, gallium arsenide, gallium phosphide, molybdenum and mixtures thereof.

54. The method of claim 48 wherein said electrically conducting or semi-conducting substrate is a wafer, fiber, optical fiber, pill, extrusion or pellet.

55. The method of claim 48 wherein said electrically conducting or semi-conducting substrate has an etched or lithographed surface.

56. The method of claim 48 wherein said inorganic oxide composition layer is an from the group consisting of silica, alumina, titania, germania, zirconia, magnesia, gallia and mixtures thereof.

57. The method of claim 48 wherein said inorganic oxide completion layer has a thickness in the range of about 0.001 microns to about 100 microns.

58. The method of claim 48 wherein said inorganic oxide composition layer is not of a thickness to be sufficiently insulating so as to inhibit an electrical change in said inorganic crystalline composition layer from affecting charge carrying species of said electrically conducting or semi-conducting substrate.

59. The method of claim 48 wherein said inorganic crystalline composition layer is a molecular sieve selected from the group consisting of zeolitic molecular sieves, silica molecular sieves or non-zeolitic molecular sieves and mixtures thereof.

60. The method of claim 59 wherein said molecular sieve includes at least one organic agent.

61. The method of claim 59 wherein said molecular sieve is substantially free of organic templating agent.

62. The method of claim 59 wherein said molecular sieve is selected from the group consisting of an A-type zeolitic molecular sieves, X-type zeolitic molecular sieves, Y-type zeolitic molecular sieves, L-type zeolitic molecular sieves, F-type zeolitic molecular sieves, W-type zeolitic molecular sieves, LZ-202, LZ-105 and mixtures thereof.

63. The method of claim 59 wherein said molecular sieve is a silica molecular sieve selected from the group consisting of silicalite, silicalite II, fluoride silicalite and mixtures thereof.

64. The method of claim 59 wherein said molecular sieve is a silica molecular sieve selected from the group consisting of silicalite, silicalite II, fluoride silicalite and mixtures thereof.

65. The method of claim 59 wherein said molecular sieve is a non-zeolitic molecular sieve having an empirical chemical composition on an anhydrous basis expressed by the formula I:

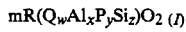

$$mR(Q_wAl_xP_ySi_z)O_2 \quad (I)$$

where
"Q" represents
(a) at least one element present as a framework oxide unit "$QO_2^n$" with charge "n" where "n" may be $-3, -2, -1, 0$ or $+1$;
  (i) a mean "T—O" distance in tetrahedral oxide structure between about 1.51 Å and about 2.06 Å
  (ii) a cation electronegativity between about 125 kcal/gm-atom to about 310 kcal/gm-atom and
  (iii) the capability of forming stable Q—O—P, Q—O—Al or Q—)—Q bonds in crystalline three dimensional oxide structures having a "Q—O" bond dissociation energy greater than about 59 kcal/gm-atom at 298° K.;
"R" represents at least one organic templating agent present in the intracrystalline pore system;
"m" represents the molar amount of "R" present per mole of $(Q_wAl_xP_ySi_z)O_2$ and has a value from zero to about 0.3; and "w", "x", "y" and "z" represent the mole fractions of $QO_2^n$, $AlO_2-$, $PO_2+$, $SiO_2$, respectfully, present as framework oxide units; and the mole fractions of "Q"; aluminum, phosphorus and silicon, respectively, present as framework oxides said mole fractions being within the following limiting compositional values:
w is equal to 0 to 98 mole percent;
y is equal to 1 to 99 mole percent;
x is equal to 1 to 99 mole percent, and
z is equal to 0 to 98 mole percent.

66. The method of claim 65 wherein said non-zeolitic molecular sieve is selected from the group consisting of AlPO$_4$, SAPO, MeAPO, MeAPSO, ELAPO and ELAPSO molecular sieves and mixtures thereof.

67. The method of claim 48 wherein said inorganic crystalline molecular sieve composition layer has a thickness in the range of about 500 Å to about 100 microns.

68. The method of claim 48 wherein said inorganic crystalline molecular sieve composition layer is of sufficient thickness so that an electrical change in the inorganic crystalline composition layer affects charge carrying species of the electrically conducting or semi-conducting substrate.

69. The method of claim 48 composite composition comprises (i) a silicon or aluminum substrate and (ii) a silicon dioxide of aluminum oxide layer upon at least a portion of the surface of said silicon or aluminum substrate.

70. The method of claim 69 wherein said molecular sieve is selected from the group consisting of zeolitic molecular sieves, silica molecular sieves, non-zeolitic molecular sieves and mixtures thereof.

* * * * *